United States Patent
Mitchell et al.

(10) Patent No.: US 8,686,724 B2
(45) Date of Patent: Apr. 1, 2014

(54) SYSTEM FOR EMULATING NUCLEAR MAGNETIC RESONANCE WELL LOGGING TOOL DIFFUSION EDITING MEASUREMENTS ON A BENCH-TOP NUCLEAR MAGNETIC RESONANCE SPECTROMETER FOR LABORATORY-SCALE ROCK CORE ANALYSIS

(71) Applicant: Schlumberger Technology Corporation, Sugar Land, TX (US)

(72) Inventors: Jonathan Mitchell, Cambridgeshire (GB); Edmund J. Fordham, Kedington (GB)

(73) Assignee: Schlumberger Technology Corporation, Sugar Land, TX (US)

(*) Notice: Subject to any disclaimer, the term of this patent is extended or adjusted under 35 U.S.C. 154(b) by 0 days.

(21) Appl. No.: 13/802,091

(22) Filed: Mar. 13, 2013

(65) Prior Publication Data
US 2013/0265055 A1    Oct. 10, 2013

Related U.S. Application Data

(62) Division of application No. 12/731,005, filed on Mar. 24, 2010, now Pat. No. 8,427,145.

(51) Int. Cl.
G01V 3/00    (2006.01)
G01V 3/18    (2006.01)

(52) U.S. Cl.
USPC ............... 324/303; 324/307; 324/309; 702/9

(58) Field of Classification Search
USPC .......................................... 324/303; 702/6–9
See application file for complete search history.

(56) References Cited

U.S. PATENT DOCUMENTS

| | | | |
|---|---|---|---|
| 5,023,551 A | 6/1991 | Kleinberg et al. |
| 5,055,788 A | 10/1991 | Kleinberg et al. |
| 5,212,447 A | 5/1993 | Paltiel |
| 5,525,904 A | 6/1996 | Hanley et al. |
| 5,796,252 A | 8/1998 | Kleinberg et al. |

(Continued)

OTHER PUBLICATIONS

P.C. Hansen, "Analysis of discrete ill-posed problems by means of the L-curve," SIAM Rev., vol. 34, No. 4, Dec. 1992, pp. 561-580.

(Continued)

*Primary Examiner* — Jermele M Hollington
*Assistant Examiner* — Emily Chan
(74) *Attorney, Agent, or Firm* — Jay P. Sbrollini; Wayne I. Kanak

(57) ABSTRACT

A laboratory NMR methodology (and corresponding laboratory apparatus) defines a sample volume. The method stores downhole tool data corresponding to a hydrocarbon-bearing sample collected from a given subsurface formation. The downhole tool data includes parameters pertaining to magnetic fields used by a downhole tool during a suite of NMR measurements of the given subsurface formation. The sample is positioned in the sample volume of the laboratory apparatus, which applies a static magnetic field in the sample volume. Furthermore, the laboratory apparatus applies a suite of NMR measurements to the sample volume to thereby determine a property of the sample. The NMR measurements of the suite each include a pulse sequence of oscillating magnetic field in conjunction with a pulsed-mode gradient field. The pulsed-mode gradient field is based on the stored downhole tool data corresponding to the sample. A laboratory NMR methodology for optimizing downhole NMR measurements is also described.

25 Claims, 13 Drawing Sheets

(56) References Cited

U.S. PATENT DOCUMENTS

| | | | |
|---|---|---|---|
| 6,229,303 | B1 | 5/2001 | Guzik |
| 6,229,308 | B1 | 5/2001 | Freedman |
| 6,346,813 | B1 | 2/2002 | Kleinberg |
| 6,462,542 | B1 | 10/2002 | Venkataramanan et al. |
| 6,570,382 | B1 | 5/2003 | Hurlimann et al. |
| 6,597,171 | B2 | 7/2003 | Hurlimann et al. |
| 6,859,032 | B2 | 2/2005 | Heaton et al. |
| 6,891,369 | B2 | 5/2005 | Hurlimann et al. |
| 6,937,014 | B2 | 8/2005 | Sun et al. |
| 6,960,913 | B2 | 11/2005 | Heaton |
| 7,034,528 | B2 | 4/2006 | Minh et al. |
| 7,040,815 | B2 | 5/2006 | Hsu |
| 7,053,611 | B2 | 5/2006 | Freedman |
| 7,180,288 | B2 | 2/2007 | Scheven |
| 7,253,618 | B1 | 8/2007 | Freedman et al. |
| 7,417,426 | B2 * | 8/2008 | Race et al. .......... 324/303 |
| 7,486,070 | B2 | 2/2009 | Madio et al. |
| 7,952,352 | B2 * | 5/2011 | Ogawa et al. .......... 324/307 |
| 2005/0270023 | A1 * | 12/2005 | Freedman .......... 324/303 |
| 2007/0108982 | A1 * | 5/2007 | Potter .......... 324/356 |
| 2008/0315873 | A1 | 12/2008 | Ganesan |
| 2009/0093962 | A1 | 4/2009 | Akkurt |
| 2009/0167302 | A1 | 7/2009 | Edwards et al. |
| 2009/0179636 | A1 * | 7/2009 | Chen .......... 324/303 |

OTHER PUBLICATIONS

J.P. Butler et al., "Estimating Solutions of First Kind Integral Equations with Nonnegative Constraints and Optimal Smoothing," SIAM Journal on Numerical Analysis, vol. 18, No. 3, 1981, pp. 381-397.

G. Wahba, "Practical Approximate Solutions to Linear Operator Equations When the Data are Noisy," SIAM Journal on Numerical Analysis, vol. 14, 1977, pp. 651-667.

J.D. Wilson, "Statistical Approach to the Solution of the First Kind Integral Equations Arising in the Study of Materials and their Properties," Journal of Materials Science, vol. 27, Jul. 1992, pp. 3911-3924.

W.S. Price, "Pulse-field Gradient Nuclear Magnetic Resonance as a Tool for Studying Translational Diffusion: Part II. Experimental Aspects," Concepts in Magnetic Resonance, vol. 10, 1998, pp. 197-237.

M.D. Hurlimann, L. Venkataramanan, C. Flaum, "The diffusion-spin relaxation time distribution function as an experimental probe to characterize fluid mixtures in porous media," J. Chem, Phys, vo. 117, pp. 10223-10232, 2002.

M.D. Hurlimann, L. Venkataramanan, "Quantitative measurement of two-dimensional distribution functions of diffusion an drelaxation in grossly inhomogeneous fields," J. Magn. Reson., vol. 157, pp. 31-42, 2002.

G. Leu, E.F. Fordham, M.D. Hurlimann, P. Frulla, "Fixed and pulsed gradient diffusion methods in low-field core analysis," Magn, Reson, Imaging, vol. 23, pp. 305-309, 2005.

H. Carr, E. Purcell, "Effects of diffusion on free precession in NMR experiments," Phys, Rev., vol. 94, pp. 630-638, 1954.

Meiboom, Gill, "Modified Spin-echo Method for Measuring Nuclear Relaxation Times," Rev. Sci. Instrum., vol. 29, pp. 688-691, 1958.

L. Venkataramanan, Y.Q. Song, M.D. Hulimann, "Solving fredholm integrals of the first kind with tensor product structure in 2 and 2.5 dimensions," IEEE Trans. Sig. Process., vol. 50, pp. 1017-1026, 2002.

Y.Q. Song, L. Venkataramanan, M.D. Hulimann, M. Flum, Pi Frulla, C. Straley, "T1—T2 correlation spectra obtained using a fast two-dimensional Laplace inversion," J. Magn, Reson., vol. 154, pp. 261-268, 2002.

E.L. Hahn, "Spin echoes," Phys, Rev., vol. 80, pp. 580-594, 1950.

A.A. Istratov, O.F. Vyvenko, "Exponential analysis in physical phenomena," Rev. Sci Instrum., vol. 70, pp. 1233-1257, 1999.

Scheven, Stray Field Measurements of Flow Displacement Distributions Without Pulsed Field gradients, Journal of Magnetic Resonance 174 (2050)338-342.

Lamb, et al, "Fixed Field Gradient NMR Diffusion Measurements Using Bessel Function Fits to the Spin-Echo Signal," Journal of Magnetic Resonance 72 (1987) 532-539.

* cited by examiner

SYSTEM FOR EMULATING NUCLEAR MAGNETIC RESONANCE WELL LOGGING TOOL DIFFUSION EDITING MEASUREMENTS ON A BENCH-TOP NUCLEAR MAGNETIC RESONANCE SPECTROMETER FOR LABORATORY-SCALE ROCK CORE ANALYSIS

BACKGROUND OF THE INVENTION

1. Field of the Invention

This invention relates to laboratory and borehole instruments making use of nuclear magnetic resonance (NMR) techniques for evaluating characteristics of hydrocarbon-bearing formations.

2. Description of Related Art

The introduction of pulsed nuclear magnetic resonance (NMR) logging tools in the early 1990s has provided the oil and gas industry with powerful new methods for evaluating petroleum reservoirs. The initial applications of pulsed NMR logging tools were aimed at providing important rock quality properties such as lithology-independent total porosity, free- and bound-fluid porosity, and permeability.

As is well known, the rate of decay of the NMR signal can be described, for example, by a distribution of decay times, which are called transverse relaxation times ($T_2$). It is customary to fit the measured NMR signals to a sum of several decaying single-exponential signals, each with amplitude and associated decay time $T_2$. The fitting procedure is achieved by a mathematical technique known as inversion.

The measurement of diffusion has become an important function of NMR well logging devices. NMR signals are attenuated by the molecular diffusion of oil, gas, and brine molecules through gradients in the static magnetic field. This effect is the physical mechanism that underlies all stand-alone NMR fluid characterization methods. Molecular diffusion is the random motion of molecules. The molecular diffusion constant of a molecule determines the mean square distance that the molecule will move per unit time. The diffusion of gas and water molecules can be described by a single molecular diffusion constant. Crude oils, on the other hand, have distributions of molecular diffusion constants that reflect the diversity of molecular sizes among the various components. Small, lightweight molecules like methane and ethane are relatively mobile in the gas phase and have molecular diffusion constants (D) that are typically about an order of magnitude greater than those of water molecules. In contrast, intermediate-to-high-viscosity crude oils have molecular diffusion constants that are much smaller than those of water. Contrasts in the molecular diffusion constants of formation fluids are exploited by using specially designed NMR measurements that are sensitive to diffusion. The NMR measurements carried out by the NMR well logging device can utilize fixed field gradient protocols. The NMR data are then analyzed to provide oil, gas, and brine saturations.

Bench-top NMR analysis is also commonly carried out in a petrophysical laboratory setting where rock core samples are subject to NMR measurements that are sensitive to diffusion. Such laboratory NMR measurements typically utilize a homogeneous static magnetic field profile together with a pulsed magnetic field gradient generated by application of direct current through gradient coils placed in close proximity to the sample volume. Typically, the protocols utilized by the bench-top NMR analysis in the petrophysical laboratory setting are different in many respects from those carried out by NMR well logging devices due to:

the more homogeneous nature of the static magnetic field of the bench-top NMR analysis as compared to the static magnetic field of the NMR well logging device;

the preferred use of pulsed field gradients as opposed to fixed field gradients; and the preferred use of constant time/variable gradient strength diffusion encoding as opposed to variable time/constant gradient strength diffusion encoding.

Because bench-top NMR analysis typically utilizes a different protocol than NMR well logging devices, it is difficult to directly compare the NMR data produced by an NMR well logging device and bench-top NMR analysis with regard to a given formation sample.

BRIEF SUMMARY OF THE INVENTION

The present invention allows for direct comparison of the NMR data sets produced by an NMR well logging tool and bench-top NMR analyzer for a given formation sample. In accordance with the invention, a method is provided for use in conjunction with a laboratory apparatus defining a sample volume. The method stores downhole tool data corresponding to a sample (e.g., rock core sample) collected from a given subsurface formation. The downhole tool data includes parameters pertaining to time-varying magnetic fields used by a downhole tool during NMR measurements of the given subsurface formation as well as NMR log data derived from such NMR measurements. The sample is positioned in the sample volume of the laboratory apparatus. The laboratory apparatus applies NMR measurements to the sample volume to determine a petrophysical property of the sample. The NMR measurements employ a homogeneous static magnetic field in the sample volume as well as a pulse sequence of oscillating magnetic field in conjunction with a pulsed-mode gradient field. The pulsed-mode gradient field is based on the stored downhole tool data corresponding to the sample (i.e., the parameters for the NMR measurements carried out by the downhole tool in deriving the NMR log data for the region of the formation corresponding to the sample). The NMR measurements carried out by the laboratory apparatus and the NMR data derived therefrom can be directly compared to the NMR data sets produced by the NMR well logging tool.

The direction comparison of NMR data sets produced by an NMR well logging tool and bench-top NMR analyzer can be used to calibrate the petrophysical interpretations made of borehole logging measurements, because in the laboratory the operator has access to independent measurements on the same rock and fluid samples. These measurements include (but are not limited to) porosity, pore size distribution, permeability, oil and water saturations, oil viscosity, and indicators of crude oil chemical composition, all of which petrophysical properties influence the NMR signal acquired, and for all of which there are known methods of interpretation in the prior art. The importance of reference measurements arises because most of these interpretation methods (whether for rock properties or for fluid properties) are subject to uncertainties and ambiguities, both in data processing and in the physics of the NMR response, where different rock or fluid properties may give rise to a similar NMR signal or signature. Having access to actual rock and fluid samples in the lab, on which such properties can be determined with much less ambiguity, is thus of great value in interpreting the borehole NMR logs. For some applications, it becomes important to carry out the laboratory NMR measurements under conditions as close as possible to those obtaining in the actual logging tool, because different biases occur for different NMR protocols, and because signal-to-noise ratio may be radically different between laboratory and borehole.

In an exemplary embodiment, the pulse sequence of oscillating magnetic field includes an initial tipping radio frequency (RF) pulse and at least one re-focusing RF pulse, and the nuclear magnetic resonance measurements of the suite each receive at least one spin echo from the sample volume for recordation and analysis. The amplitude of the at least one spin echo is modified by the pulsed field gradient so as to be encoded for diffusion.

In the preferred embodiment, the downhole tool employs a fixed magnetic field gradient that has constant amplitude at all times. In the laboratory apparatus, the pulsed mode gradient field for a given NMR measurement is defined by a set of pulses that are equivalent to the fixed field gradient for a corresponding measurement performed by the downhole tool. In an exemplary embodiment, the set of pulses are each characterized by a uni-polar half-sine waveform. The set of pulses are preferably defined by selecting at least one parameter (e.g., maximum amplitude and/or pulse duration) associated therewith such that the integral of the time-varying amplitude of the pulses of the set over the time duration of the pulses of the set matches the product of the constant amplitude of the fixed field gradient and duration for the corresponding measurement performed by the downhole tool.

Moreover, the pulse duration for the set of gradient pulses can be constrained by the spacing between an initial tipping pulse and a subsequent re-focusing pulse. This constraint ensures that the gradient pulses do not overlap in time with the pulses of oscillating magnetic field (as well as the receive mode time periods for acquisition of the measured resonance signal). This feature provides the following advantages:

1) the spin dynamics are simplified; notably the application of the pulses of oscillating magnetic field does not generate off-resonance effects such as stimulated echoes; and 2) the spin echoes are not narrowed significantly by magnetic field inhomogeneities, providing a longer receive mode acquisition window and hence improved signal-to-noise ratio.

These advantages simplify the data acquisition and analysis.

In the preferred embodiment, the suite of NMR measurements performed by the laboratory apparatus are processed by an inversion methodology that derives a two-dimensional distribution function $f(D,T_2)$ relating diffusion coefficient D to the spin-spin ($T_2$) relaxation times of the hydrocarbon-bearing sample.

The invention can also be used in a predictive manner to plan a logging program not yet undertaken. In this scenario, the laboratory measurements can be carried out with various choices of parameter, in order to predict the likely response of the rock formations to the NMR logging measurements, and to determine, design, or otherwise optimize the parameter selections required to yield the necessary precision, resolution, or other discrimination required in the measurements for which the borehole logging program is undertaken. This can be done, for example, when rock or fluid samples from the same or a similar rock formation are available already, and are believed to possess properties representative of the formation to be studied. Laboratory measurements on such samples can be done to plan the best choice of protocols or parameters that can be made in advance of performing the actual borehole measurements. Having determined an optimum choice of protocol or parameter in the laboratory, these parameters are then transferred to the logging tool when the borehole measurements are made.

A similar planning exercise can be made in preparing for borehole measurements in the observation wells in connection with enhanced oil recovery (EOR) projects. More particularly, an NMR logging tool can be used to monitor the progress of an EOR project, where injection of gases such as carbon dioxide, methane, or mixtures of such gases with other light hydrocarbons may be used to improve the displacement and recovery of reservoir hydrocarbon. Alternative EOR processes may involve the use of chemical surfactants to improve oil recovery by reducing surface tension and detergency. It is normal practice to introduce observation wells in such projects, which are drilled primarily to monitor the process rather than for producing oil, or injecting the gases or surfactants. NMR is one technology that can be used for such observations, provided the wells are cased with tubulars which are invisible to NMR. An example of such observation wells is described in Patent Publication US 2009/0167302. However, because of the cost of drilling and completing such wells, before the engineering and financial commitment is made, it is important to be able to predict by laboratory study that measurements performed in the borehole will in fact yield the necessary data to perform the required monitoring.

In such observation wells the basic formation properties will be well-known by coring and logging programs at the time the well is drilled, and from other known information regarding the hydrocarbon-bearing reservoir. In the observation well, it is important to be able to detect and measure changes not in rock properties (which are of course unlikely to change radically) but in fluid properties and fluid content, most obviously in oil saturation remaining at various times during the EOR project. In such applications, it is important to be able to choose protocols, parameter settings, and averaging times (or number of repeat measurements required) such that the desired accuracy, resolution, or discrimination in the changes in fluid content or properties will be achieved. In this application, the laboratory measurements may need to be carried out using various different oil saturation states, using a sample holder (core holder) capable of changing the saturation of oil or other fluids by various flow processes. The rock core sample will be chosen to be representative of the most important parts of the rock formation penetrated by the observation well, or may include several such samples in the laboratory measurements. Also, the measurements will probably need to be carried out at temperatures and pressures representative of the actual reservoir because the NMR properties of the fluids will change with temperature and pressure. The importance of the present invention in this application comes from the ability to predict in advance that changes in oil saturation can be observed with the borehole tool, with the required degree of accuracy, and taking into account the signal-to-noise ratio expected from the tool in the borehole, and the data processing methods that will be used. The best confidence in such planning will come from laboratory measurements that mimic the borehole tool as closely as possible, take account of the signal-to-noise ratio available in the tool (or plan for a necessary degree of averaging) and employ the same data processing methods.

In observation wells of the kind cited there is also a need to plan the protocols that will be used. Borehole logging in observation wells is subject to fewer practical constraints that in "open hole" wells (without casing). In particular, the presence of a casing eliminates the risk of a tool becoming stuck in the mudcake that adheres to the exposed rock surface in an open hole. Also, because the observation well has no other purpose, the length of time that the tool spends in the borehole does not have the same economic cost on impeding other operations. Therefore, the tool can stop for as long as necessary, or employ NMR protocols of long duration that are feasible in the laboratory, but not ordinarily feasible in open-hole borehole logging because of the need for the tool to move continuously, and to minimize overall well log duration.

Additional objects and advantages of the invention will become apparent to those skilled in the art upon reference to the detailed description taken in conjunction with the provided figures.

DETAILED DESCRIPTION OF THE INVENTION

Figure 1:
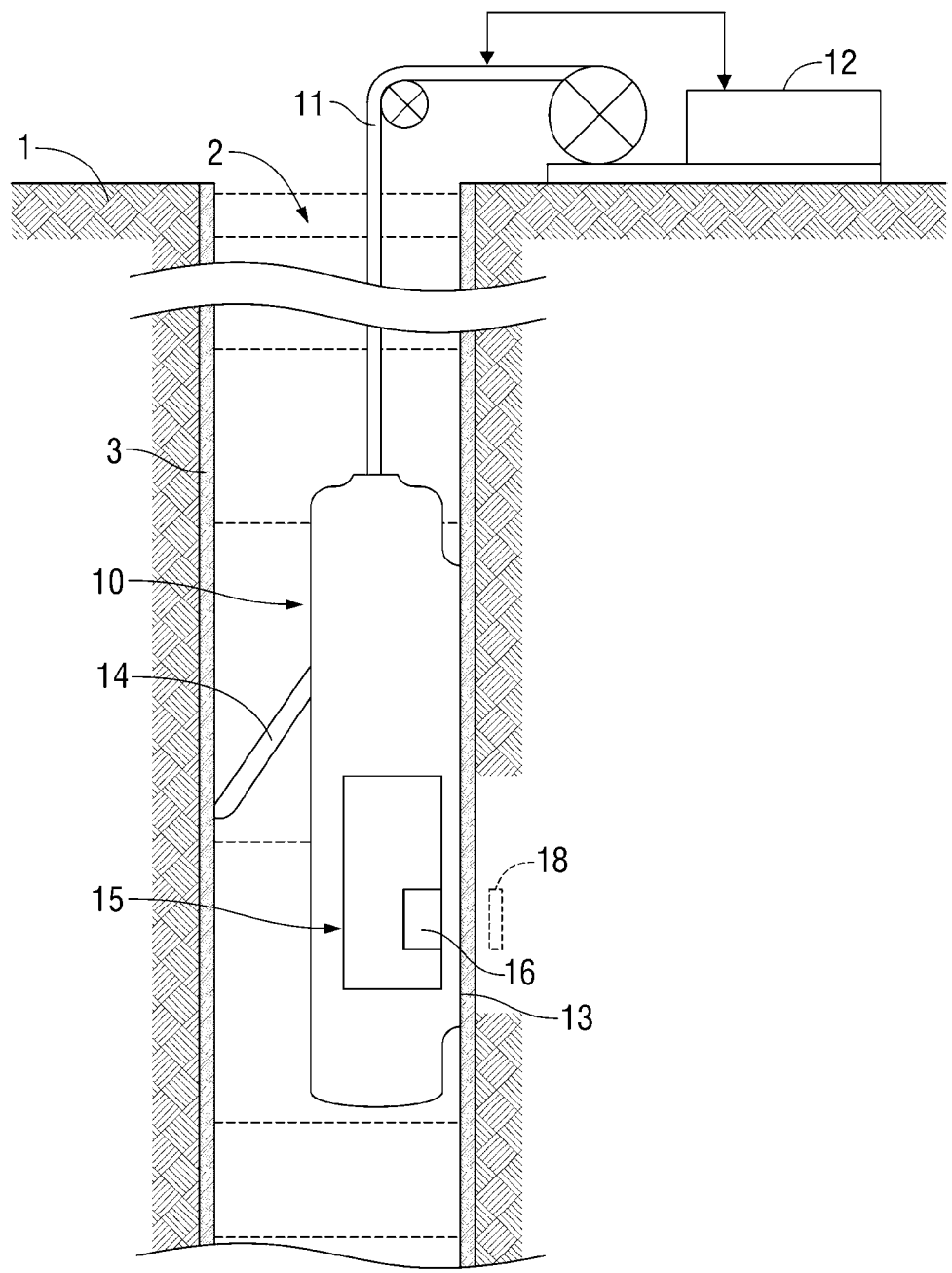
FIG. 1 shows an NMR well logging tool which can be used in practicing an embodiment of the present invention.

Embodiments of the invention relate to apparatus and methods for determining reservoir fluid properties using an NMR well logging tool. FIG. 1 shows an exemplary apparatus for investigating a subsurface formation 1 traversed by a borehole 2. The borehole 2 is typically, although not necessarily, filled with a drilling fluid or mud (which contains finely divided solids in suspension) with mudcake 3 on the walls of the borehole. A downhole logging tool 10 is suspended in the borehole 2 on an armored cable 11, the length of which substantially determines the relative depth of the logging tool 10. The cable length is controlled by suitable means at the surface such as a drum and winch mechanism (not shown). Surface equipment, represented at 12, can be of conventional type, and can include a processor subsystem and communicates with the logging tool 10. The logging tool 10 has a face 13 shaped to intimately contact the borehole wall, with minimal gaps or standoff, and a retractable arm 14 which can be activated to press the body of the logging tool 10 against the borehole wall during a logging run, with the face 13 pressed against the wall's surface. Although the logging tool 10 is shown as a single body, the tool may alternatively comprise separate components such as a cartridge, sonde, or skid, and the tool may be combinable with other logging tools. Also, while a wireline tool is illustrated, alternative forms of physical support and communicating link can be used, for example in a measurement-while-drilling system.

Figure 2:
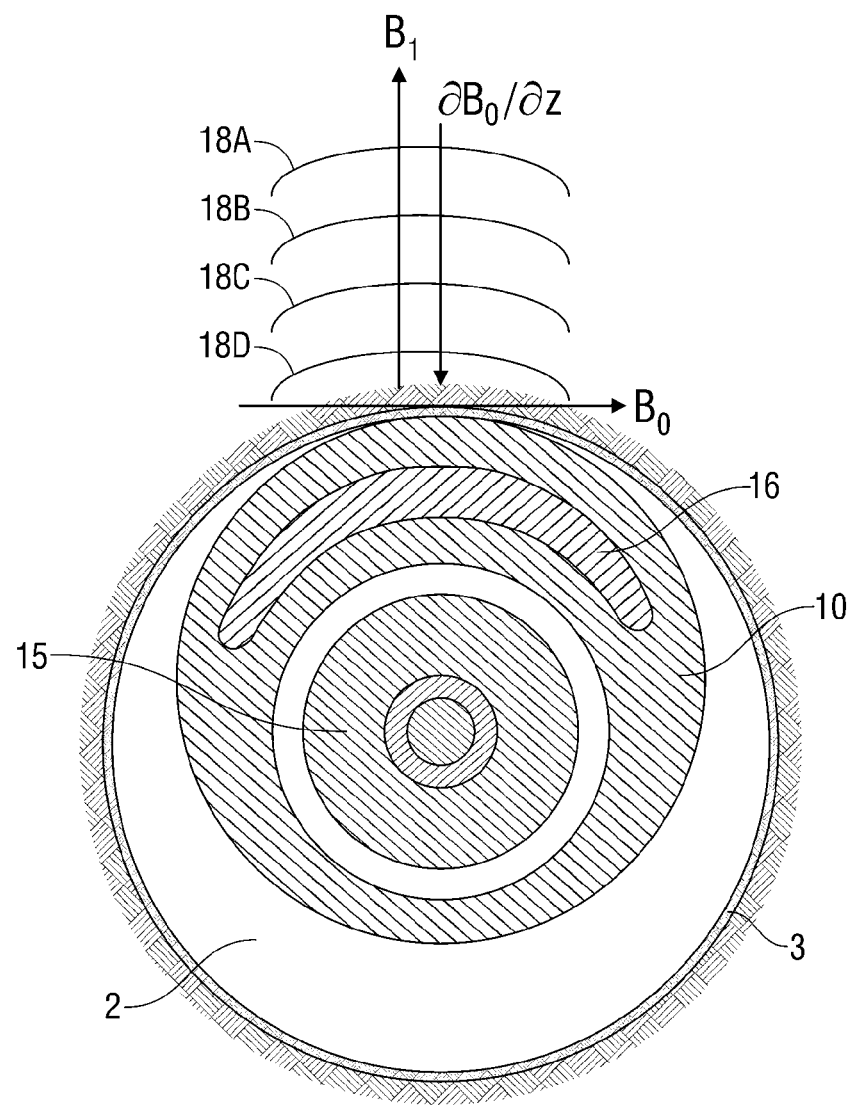
FIG. 2 is a cross-sectional view of a portion of the NMR well logging tool of FIG. 1

In an exemplary embodiment, the logging tool 10 is the MR Scanner tool available from Schlumberger Technology Corporation of Sugar Land, Tex., USA and described in U.S. Pat. No. 7,486,070, which is incorporated herein by reference. As shown in FIG. 2, logging tool 10 includes a permanent magnet assembly 15 as well as an array of radio frequency (RF) antennae (one shown as 16) positioned between permanent magnet assembly 15 and the wall engaging face 13. The permanent magnet assembly 15 produces a static magnetic field $B_0$ in a sample volume 18. The sample volume 18 is a region directly in front of tool face 13. Thus, during use, the sample volume 18 lies within the formation 1 as shown. The static magnetic field $B_0$ is inhomogeneous due to the design of the permanent magnet assembly 15 and thus produces a spatial magnetic field gradient ($\partial B_0/\partial z$) in the sample volume 18. The RF antenna 16 radiates, at selected times, an oscillating RF magnetic field $B_1$ having a magnetic moment substantially perpendicular (orthogonal) to that of the static magnetic field $B_0$ produced by the permanent magnet assembly 15 as indicated by the arrows shown in FIG. 2. One of ordinary skill in the art would appreciate that the same RF antenna 16 may function as a transmitter to transmit the oscillating magnetic field and as a receiver to receive the signals. Alternatively, separate transmitter and receiving antennas may be used. The logging tool 10 is capable of carrying on NMR analysis at multiple depths of interest in thin shells, such as shells 18A, 18B, 18C, and 18D as shown. Advantages of using the logging tool of FIG. 2 may include, but are not limited to, the ability to assess various and multiple depths of interest, the ability to probe deeper into a rock formation, sensing of a large region, and easier tuning. Though shown as being placed adjacent the borehole wall, the logging tool 10 may perform measurements in positions offset from the borehole wall (e.g., in the center of the borehole).

The logging tool 10 can be used to make NMR measurements related to the diffusion and relaxation properties of fluid samples. Because these properties are generally different for oil and water, these measurements can provide a means for determining the relative proportion of water and oil in a fluid sample. In addition, these measurements can provide information on the properties of the oils, including their compositions, viscosities and gas/oil ratios (amounts of solution gas contained in the oil). Similarly, for a fluid sample, which may comprise (1) gas and water, (2) gas, oil, and water, (3) oil and gas, or (4) oil and water, the measurements can provide a means for determining the relative proportions of the different components that are present. In addition, these measurements can provide information on the hydrocarbon properties that are important for determining the monetary value of the reservoir and also essential for making well completion decisions.

The NMR measurements carried out by the logging tool 10 are based on well known principles that have become an important tool in formation evaluation. General background of NMR formation evaluation can be found, for example, in U.S. Pat. No. 5,023,551, which is incorporated herein by reference. The NMR measurements rely upon the fact that the nuclei of many chemical elements have angular momentum ("spin") and a magnetic moment. In an externally applied static magnetic field $B_0$, the spins of nuclei align themselves along the direction of the static magnetic field $B_0$. This equilibrium situation can be disturbed by a pulse of an oscillating magnetic field $B_1$ that tips the spins away from the direction of the static magnetic field $B_0$. For example, if a pulse of alternating current having a frequency f is passed through an RF antenna coil producing the oscillating polarizing magnetic field $B_1$ perpendicular to the static magnetic field $B_0$, a population of nuclei precessing at the Larmor frequency equal to f align at angle θ relative to the $B_0$ direction. At the end of the pulse, when the polarizing magnetic field $B_1$ is removed, the aligned nuclei experience a perpendicular torque, and precess about the $B_0$ vector. After a characteristic time called the longitudinal or spin-lattice relaxation time $T_1$, the nuclei relax to the thermal equilibrium, where a weighted percentage of the nuclei are aligned in the $B_0$ direction. The angle θ is given by $\theta=\gamma B_1 t_p/2$, where γ is the gyromagnetic ratio, $B_1$ is the linearly polarized oscillating field strength, and $t_p$ is the duration of the pulse. Pulses that produce an angle θ of ninety degrees (referred to as a "90-degree pulse") are common.

Also associated with the spin of molecular nuclei is a second relaxation time, $T_2$, called the spin-spin relaxation time. At the end of a 90-degree pulse, all the spins are pointed in a common direction perpendicular, or transverse, to the $B_0$ direction, and they all precess at the Larmor frequency. However, because of small fluctuations in the static field induced by other spins, paramagnetic impurities and the inhomogeneity of the static $B_0$ field, the spins precess at slightly different frequencies, and the transverse magnetization dephases with a time constant referred to as the spin-spin relaxation time $T_2$.

A standard technique for measuring the spin-spin relaxation time $T_2$ utilizes an RF pulse sequence known as the CPMG (Carr-Purcell-Meiboom-Gill) sequence. As is well known, after a wait time that precedes each pulse sequence, a 90-degree pulse is emitted by the RF antenna 16, which causes the spins to start precessing in the transverse plane. After a delay, an initial 180-degree pulse is emitted by the RF antenna 16. The initial 180-degree pulse causes the spins, which are dephasing in the transverse plane, to reverse direction and to refocus and subsequently cause an initial spin echo to appear. A second 180-degree refocusing pulse can be emitted by the RF antenna 16, which subsequently causes a second spin echo to appear. Thereafter, the RF antenna 16 emits a series of 180-degree pulses separated by a short time delay. This series of 180-degree pulses repeatedly reverse the spins, causing a series of "spin echoes" to appear. The train of spin echoes is measured and processed to determine the spin-spin relaxation time $T_2$.

In a uniform static magnetic field, each spin will experience the same magnetic field strength regardless of its position within the static field, and diffusion will not contribute to the observed spin-spin relaxation time $T_2$. However, in the magnetic field gradient of the inhomogeneous static magnetic field $B_0$, each spin will experience different magnetic field strengths as it diffuses through the static field. The Larmor frequencies of the diffusing spins become time dependent, and the 180-degree pulses cannot refocus the spins completely, leading to an additional decay. This additional decay contributes to the observed spin-spin relaxation time $T_2$ and is dependent on the diffusion coefficient D of the fluid, the magnitude and duration of the magnetic field gradient, and the magnitude of the static magnetic field. As the diffusion coefficient provides an indication of fluid type, measurement of the diffusion effects on observed spin-spin relaxation time $T_2$ can be used as the basis for determining the types of fluids in a hydrocarbon formation.

Figure 3:
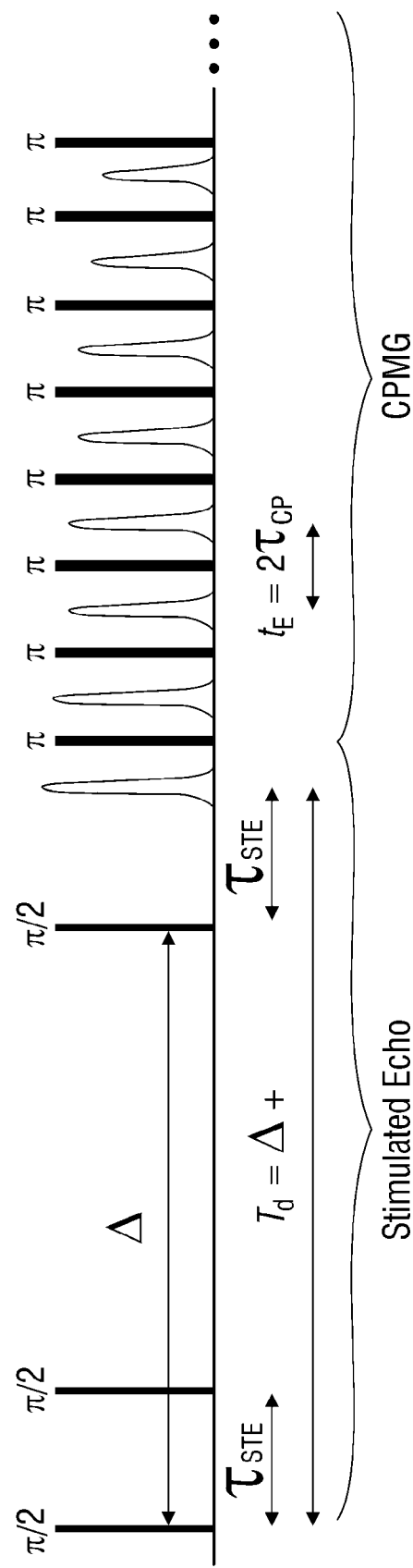
FIG. 3 is a schematic diagram illustrating an exemplary sequence of NMR excitation signals (and echo signals produced therefrom) which can be used by the NMR well logging tool of FIG. 1 in practicing an embodiment of the present invention.

NMR analysis utilizing inhomogeneous static fields in conjunction with diffusion editing by either stimulated echoes (STE) or Hahn echoes (HE) followed by a modified CPMG pulse train is also standard practice. Examples of such NMR analysis are set forth in U.S. Pat. No. 6,570,382, which is incorporated herein by reference. In an exemplary embodiment of the invention, the logging tool 10 carries out NMR analysis employing an STE sequence for diffusion editing followed by a modified CPMG pulse train as shown in FIG. 3. The STE sequence includes a series of two 90-degree pulses at times $\tau_{STE}$ and Δ after an initial 90-degree pulse, which produces a stimulated echo at time $(\tau_{STE}+\Delta)$. The time $\tau_{STE}$ is typically referred to as the spatial encoding interval, and the time Δ is typically referred to as the storage interval. The modified CPMG sequence follows the STE sequence and contains a series of 180-degree pulses that follow the stimulated echo of the STE sequence by a time $\tau_{CP}$. The 180-degree pulses refocus the stimulated echo to produce a series of spin echoes having a time spacing approximately equal to $2\tau_{CP}$. The stimulated echo produced by the STE sequence encodes for diffusion, while the spin echoes produced by the modified CPMG pulse train encode for the transverse relaxation time $T_2$ as is well known in the art. In the preferred embodiment, $\tau_{STE}$ is in the range of a few milliseconds, Δ is in the range of 50 ms to 1 second, and $\tau_{CP}$ is in the range of 100 μs to 500 μs. Other embodiments of NMR sequences that can be used in accordance with the present invention are described in U.S. Pat. No. 6,570,382.

The NMR measurements carried out by the logging tool 10 measure spin echo amplitude for one or more NMR sequences. From these measurements, the diffusion coefficient D, as well as other fluid properties of the hydrocarbon formation sample located in the sample volume 18, can be derived. The NMR measurements thus obtained are "diffusion encoded" and can be inverted to produce a multi-dimensional distribution function relating to fluid properties of the sample. The multi-dimensional distribution can be a two-dimensional (2-D) distribution function $f(D,T_2)$ relating the diffusion coefficient D to the spin-spin relaxation times $T_2$ of the sample, a 2-D distribution function $f(D,T_1)$ relating the diffusion coefficient D to the spin-lattice relaxation time $T_1$ of the sample, or a three-dimensional (3-D) distribution function $f(D,T_1, T_2)$ relating the diffusion coefficient D to the spin-lattice relaxation time $T_1$ and the spin-spin relaxation time $T_2$ of the sample. Examples of such inversion techniques are described in detail in U.S. Pat. Nos. 6,570,382; 6,960,913; and 7,053,611, herein incorporated by reference in their entireties.

For example, the multi-dimensional distribution function can be a 2-D distribution function $f(D,T_2)$ relating the diffusion coefficient D to the spin-spin ($T_2$) relaxation times of the sample. For an oil-water sample, the function $f(D,T_2)$ can be used to estimate the relative volumes of oil and water, oil viscosity, molecular composition of the oil, and gas-oil ratio. A more detailed discussion of methodologies for deriving a two-dimensional (2-D) distribution function $f(D,T_2)$ relating the diffusion coefficient D to the spin-spin ($T_2$) relaxation times of the sample as measured by the logging tool 10 is set forth below. In another example, the multi-dimensional distribution function can be derived from maximum entropy principles (MEP) methodology as described in U.S. Pat. No. 6,960,913.

For the respective NMR measurements carried out by the logging tool 10 in evaluating a formation sample, information that characterizes each respective NMR sequence (e.g., data used to program the laboratory NMR apparatus to generate a corresponding NMR sequence, such as the spatial encoding interval δ, the storage interval Δ, and the echo spacing $\tau_{CP}$ for the exemplary STE sequence of FIG. 3), as well as the NMR measurement data obtained from each respective NMR sequence and fluid information derived therefrom, can be stored in a database. This information is collectively referred to as tool-related NMR information. Alternatively, the tool-related NMR information can be input by the user during setup of the NMR analysis for a given sample. The tool-related NMR information is associated with a formation sample (e.g., rock core sample) acquired from the same formation. Preferably, the formation sample is acquired from a borehole location at or near the tool location from which the associated NMR measurement data was derived.

Figure 4:
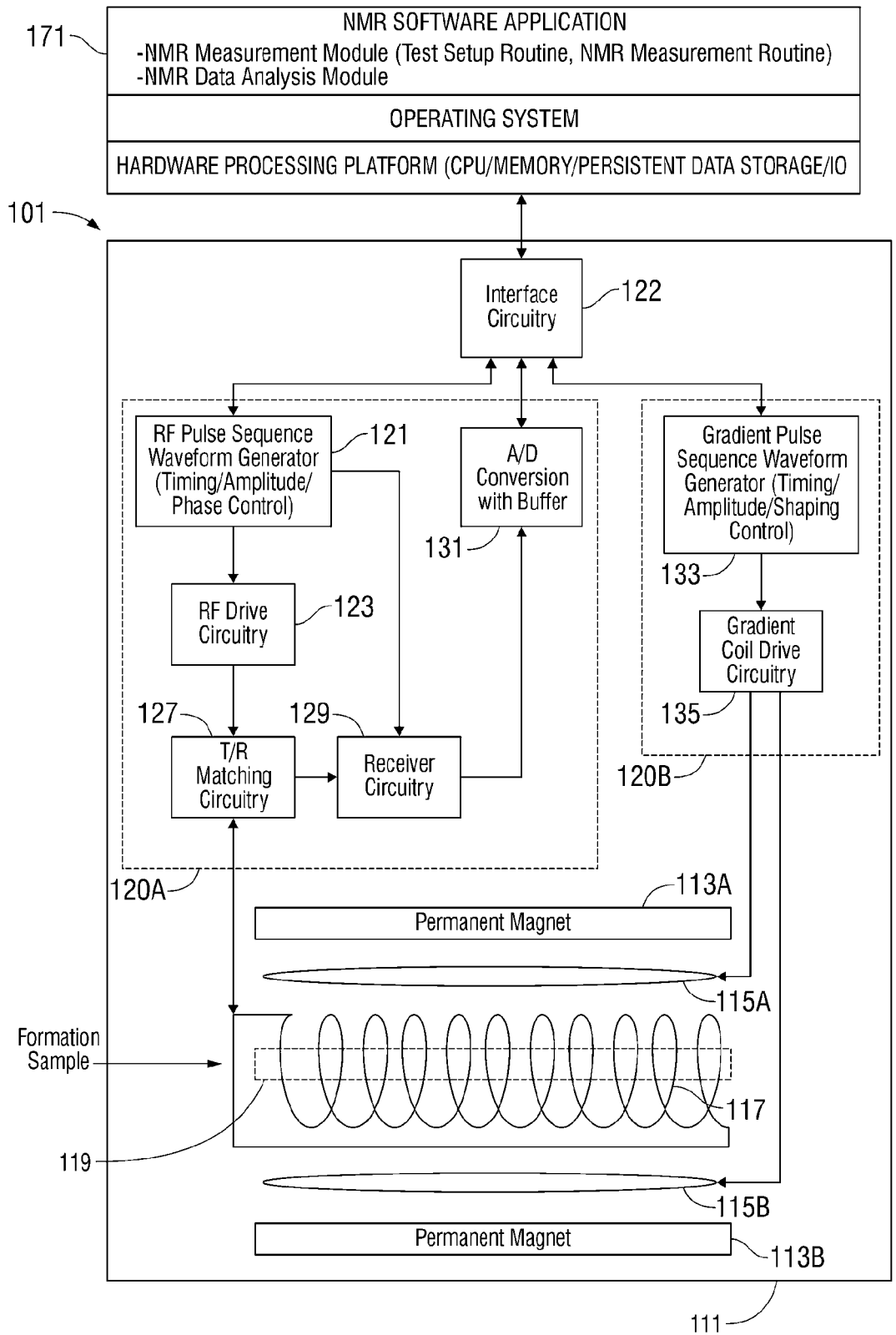
FIG. 4 is a schematic diagram of a bench-top NMR tool which can be used in practicing an embodiment of the present invention.

Turning now to FIG. 4, there is shown an apparatus 101 for carrying out laboratory NMR measurement and analysis of a hydrocarbon formation sample in accordance with a preferred embodiment of the present invention. The apparatus 101 includes an NMR instrument housing 111, which is preferably sized to rest on a standard laboratory bench-top, that houses a magnet array (e.g., permanent magnets 113A, 113B), matching gradient coils 115A, 115B, and an RF antenna 117 encompassing a sample volume 119. A formation sample of interest (e.g., rock core sample) associated with pre-existing tool-related NMR information stored in a database is selected for testing and placed in the sample volume 119. The formation sample of interest can be contained within a sample holder that is placed in the sample volume 119. A conveyor or other drive mechanism can convey the formation sample of interest through the sample volume 119 as is well known. The magnet array 113A, 113B produces a homogeneous static magnetic field $B_0$ in the sample volume 119. In the preferred embodiment, the magnetic array 113A, 113B produces a static magnetic field $B_0$ on the order of 42 mT (proton frequency of 2 MHz). Lower strength and higher strength fields can be used. Lower strength fields suffer from decreases signal-to-noise ratio. High strength fields can provide improved signal-to-noise ratio, but the measured NMR properties can be significantly different than those measured by modern NMR logging tools. The RF antenna 117 transmits pulses of an oscillating magnetic field $B_1$ across the sample volume 119. The magnetic moment of the magnetic field $B_1$ is substantially perpendicular to the static magnetic field $B_0$. The gradient coils 115A, 115B transmit a pulsed-mode magnetic field gradient $B_{PFG}$ across the sample volume 119. In an illustrative embodiment, the magnetic moment of the magnetic field gradient $B_{PFG}$ is substantially parallel to the static magnetic field $B_0$ in the sample volume 119. Note that the pulsed-mode magnetic field gradient $B_{PFG}$ can modify the homogeneous static magnetic field $B_0$ along any coordinate (x, y, z, r) in the sample volume 119.

The NMR instrument housing 111 also preferably contains electronic circuitry 120A, 120B that interfaces to the RF antenna 117 and gradient coils 115A, 115B, respectively, to carry out NMR measurements on the hydrocarbon formation sample of interest in the sample volume 119. The electronic circuitry 120A preferably operates in three modes: transmitting mode, damping mode, and receiving mode. In the transmitting mode, the RF antenna 117 is excited such that it radiates a pulse of an oscillating magnetic field $B_1$ across the sample volume 119. The pulse of oscillating magnetic field $B_1$ resonates nuclear spins in the hydrocarbon formation sample of interest disposed in the sample volume 119. Between certain pulses of the magnetic field $B_1$ produced in the transmit mode, the receive mode is carried out using the RF antenna 117 to receive oscillating magnetic signals of nuclear spin precession (also referred to as "spin echoes") radiating from the hydrocarbon formation sample of interest disposed in the sample volume 119. The damping mode is carried out between the transmit mode and receive mode in order to limit ringing of the RF antenna 117 at the end of the pulse of the oscillating magnetic field $B_1$. The electronic circuitry 120B operates to excite the gradient coils 115A, 115B such that the gradient coils radiate the controlled pulsed-mode magnetic field gradient $B_{PFG}$ across the sample volume 119 in synchronization with the pulses of oscillating magnetic field $B_1$ as described below in more detail.

In the preferred embodiment, the electronic circuitry 120A includes a circuit block 121 for generating RF pulse sequence waveforms that excite the pulses of oscillating magnetic field $B_1$ across the sample volume 119. The parameters of the RF pulse sequence waveforms are preferably controlled by control signals supplied to circuit block 121 from computer 171 via interface block 122. The RF pulse sequence waveforms generated by circuit block 121 are supplied to an RF drive circuitry 123 that amplifies the RF pulse sequence waveform to suitable power levels for supply to the RF antenna 117 in the transmit mode such that the RF antenna 117 radiates pulses of oscillating magnetic field $B_1$ oscillating at the Larmor frequency of the nucleus of interest. The Larmor frequency ω is given by, $$\omega = (\gamma B_0), \quad (1)$$

where γ is the gyromagnetic ratio of the nuclear species of interest, and $B_0$ is the strength of the static magnetic field. For hydrogen nuclei, the gyromagnetic ratio ($\gamma/2\pi$) is typically 4258 Hz/Gauss. The T/R Matching circuitry 127 provides an impedance that matches the input impedance of the RF antenna 117 in the transmit mode in order maximize power transmission to the RF antenna 117, and also provides an impedance that matches the input impedance of the receiver circuitry 129 in the receive mode in order to minimize noise. The T/R Matching circuitry 127 also provides impedance that critically dampens the RF antenna 117 in the damping mode in order to limit ringing of the RF antenna 117 at the end of the pulse of the oscillating magnetic field $B_1$. In the receive mode, the receiver circuitry 129 amplifies the signals captured by the RF antenna 117 and supplied by the T/R Matching circuitry 127, and utilizes a reference signal supplied by the circuit block 121 (this reference signal corresponds to the frequency of interest) and the amplified signal to obtain a measured NMR resonance signal at the frequency of interest from the sample volume 119. The measured NMR resonance signal is output to an analog-to-digital converter 131 for sampling and conversion into digital form. The digital data is buffered and forwarded to the computer 171 via interface block 122 for further use and analysis.

In the preferred embodiment, the electronic circuitry 120B includes a circuit block 133 for generating gradient pulse sequence waveforms that produce the pulsed-mode magnetic field $B_{PFG}$ across the sample volume 119. The parameters of the gradient pulse sequence waveforms are preferably controlled by control signals supplied to circuit block 133 from computer 171 via interface block 122. The gradient pulse sequence waveforms generated by circuit block 133 are supplied to gradient coil drive circuitry 135, which operates to amplify the gradient pulse sequence waveform generated by circuit block 133 to suitable power levels for supply to the gradient coils 115A, 115B such that the gradient coils 115A, 115B radiate pulses of magnetic field $B_{PFG}$.

The computer 171 includes a hardware processing platform that includes at least one central processing unit, memory, persistent data storage (e.g., a hard disk drive or optical disk), I/O functionality, and other functionality as is well known in the data processing arts. The persistent data storage stores an operating system and a software application (a programmed sequence of instructions) that are both loaded into memory for execution by the central processing unit(s) of the platform as is well known. In an exemplary embodiment, the computer 171 is realized by a commercially available workstation that interfaces to the NMR instrument housing 111 by a suitable interface, such as a USB or 1394 data link. The software application embodies an NMR Measurement module and an NMR Data Analysis module that carry out the laboratory NMR measurement and analysis of a hydrocarbon formation sample. The NMR Measurement module performs NMR measurements on the selected formation sample. The NMR measurements are derived from operation of a test setup routine and NMR measurement routine.

The test setup routine interfaces with the waveform generator circuit block 121 to supply the necessary parameters (e.g., pulse duration and amplitude) for programming the desired pulse sequence of oscillating magnetic field $B_1$ to be emitted by the RF antenna 117. The test setup routine also interfaces with the waveform generator circuit block 133 to supply the necessary parameters (e.g., gradient pulse timing parameters, gradient pulse amplitude parameter, gradient pulse waveform duration parameter) for programming the desired pulsed-mode magnetic field gradient $B_{PFG}$ to be emitted by the gradient coils 115A, 115B.

The NMR measurement routine triggers the electronic circuitry blocks 120A, 120B to radiate the sample volume 119 with the desired pulse sequence of oscillating magnetic field $B_1$ in conjunction with the desired pulsed-mode magnetic field gradient $B_{PFG}$ and measures and records the NMR resonance signals (e.g., including resonance spin echoes) that result therefrom.

The NMR Data Analysis module processes the NMR data recorded from one or more suites of NMR measurements carried out by the NMR Measurement module to characterize NMR-related parameters (e.g., $T_2$, D) as well as other properties of interest (e.g., relative volumes of oil and water, oil viscosity, molecular composition of the oil, and gas-oil ratio) for the selected formation sample, and store the results of NMR data analysis for the selected formation sample. Such stored results can be output (for example, presented to a user on a display screen) for comparison to NMR data analysis results derived from corresponding downhole NMR data.

The NMR measurements carried out by the NMR Measurement module measure spin echo amplitude for one or more NMR sequences. From these measurements, the diffusion coefficient D as well as other fluid properties of the hydrocarbon formation sample located in the sample volume 18 can be derived. The NMR measurements thus obtained are "diffusion encoded" and can be inverted to produce a multi-dimensional distribution function relating to fluid properties of the formation sample. The multi-dimensional distribution can be a two dimensional (2-D) distribution function $f(D,T_2)$ relating the diffusion coefficient D to the spin-spin relaxation times ($T_2$) of the formation sample, a 2-D distribution function $f(D,T_1)$ relating the diffusion coefficient D to the spin-lattice relaxation time $T_1$ of the formation sample, or a three-dimensional (3-D) distribution function $f((D,T_1, T_2)$ relating the diffusion coefficient D to the spin-lattice relaxation time $T_1$ and the spin-spin relaxation time $T_2$ of the formation sample. Examples of such inversion techniques are described in detail in U.S. Pat. Nos. 6,570,382; 6,960,913; and 7,053,611, herein incorporated by reference in their entireties.

For example, the distribution function can be a two-dimensional (2-D) distribution function $f(D,T_2)$ relating the diffusion coefficient D to the spin-spin ($T_2$) relaxation times of the sample. For an oil-water sample, the function $f(D,T_2)$ can be used to estimate the relative volumes of oil and water, oil viscosity, molecular composition of the oil, and gas-oil ratio. A more detailed discussion of methodologies for deriving a two-dimensional (2-D) distribution function $f(D,T_2)$ relating the diffusion coefficient D to the spin-spin ($T_2$) relaxation times of the sample as part of the NMR Data Analysis module is set forth below. In another example, the multi-dimensional distribution function can be derived from maximum entropy principles (MEP) methodology as described in U.S. Pat. No. 6,960,913.

In the preferred embodiment, the inversion technique carried out by the NMR Data Analysis Module of the apparatus 101 corresponds to the inversion technique utilized by the downhole tool in deriving the corresponding downhole NMR data. Such inversion processing can be loaded and/or executed as part of the NMR Data Analysis Module of the apparatus 101 in a manual manner, or possibly be loaded and/or executed as part of the NMR Data Analysis Module of the apparatus 101 in an automatic manner based on data that characterizes the inversion technique utilized by the downhole tool in deriving the corresponding downhole NMR data.

In the preferred embodiment of the invention, the oscillating magnetic field $B_1$ emitted by the RF antenna 117 of the laboratory apparatus 101 for a given pulse sequence is controlled such that the pulse sequence is equivalent to the pulse sequence applied during corresponding NMR measurements carried out downhole by the logging tool 10. Moreover, the duration and/or time-varying amplitude of the magnetic field gradient pulses emitted by the gradient coils 115A, 115B of the laboratory apparatus 101 for the given pulse sequence is controlled such that the gradient pulses are equivalent to the fixed field gradient during corresponding NMR measurements carried out downhole by the logging tool 10. The gradient pulses of a given pulse sequence are equivalent to the fixed field gradient of the logging tool 10 for a corresponding NMR sequence by ensuring that a measure of the integral of the time-varying amplitude of the gradient pulses over time is equal to the product of the magnitude of the fixed field gradient over the sequence duration for the corresponding NMR analysis.

Moreover, the gradient pulses emitted by the gradient coils 115A, 115B are applied for a controlled time duration in order to allow the magnetic field to stabilize prior to the next pulse or signal acquisition event.

Figure 5:
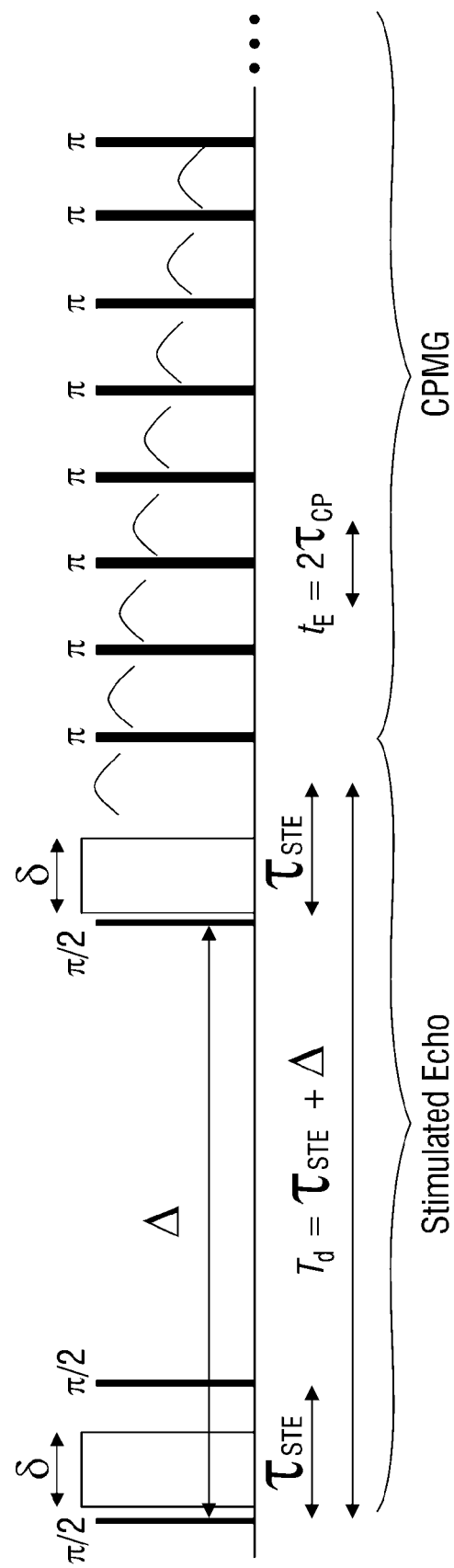
FIG. 5 is a schematic diagram illustrating an exemplary sequence of NMR excitation signals (and exemplary echo signals produced therefrom) which can be used by the bench-top NMR tool of FIG. 4 in practicing an embodiment of the present invention.

In an exemplary embodiment as shown in FIG. 5, the pulse sequence emitted by the RF antenna 117 is equivalent to that emitted by the logging tool 10 during a corresponding NMR measurement (FIG. 3), including an STE sequence and a modified CPMG sequence. The STE sequence includes a series of two 90-degree pulses at times $\tau_{STE}$ and $\Delta$ after an initial 90-degree pulse, which produces a stimulated echo at time ($\tau_{STE}+\Delta$). The modified CPMG sequence follows the STE sequence and contains a series of 180-degree pulses that follow the stimulated echo of the STE sequence by a time $\tau_{CP}$. The 180-degree pulses refocus the stimulated echo to produce a series of spin echoes having a time spacing approximately equal to $2\tau_{CP}$. The stimulated echo produced by the STE sequence encodes for diffusion, while the spin echoes produced by the modified CPMG pulse train encode for the transverse relaxation time $T_2$ as is well known in the art. The parameters $\tau_{STE}$, $\Delta$, and $\tau_{CP}$ are persistently stored by the computer 171 and loaded by the test setup routine to the waveform generator circuit block 121 for programming the desired STE pulse sequence and modified CPMG sequence of oscillating magnetic field $B_1$ to be emitted by the RF antenna 117.

During the STE sequence, the gradient coils 115A, 115B of the laboratory apparatus 101 are controlled to emit a number N of gradient pulses each defined by a like uni-polar half-sine waveform as shown. In this configuration, the integral of the time-varying amplitude of the N gradient pulses is represented mathematically as:

$$\int_0^{\delta_{PFG}} N * g_{PFG} * \sin(\pi t / \delta_{PFG}) dt = (g_{FFG} * T_d) \quad (2)$$

where N is the number of gradient pulses, $\delta_{PFG}$ is the time duration of the uni-polar half-sine waveform for each gradient pulse, $g_{PFG}$ is the maximum amplitude for the uni-polar half-sine waveform for each gradient pulse, $g_{FFG}$ is the amplitude of the fixed field gradient, and $T_d$ (i.e., $\tau_{STE}+\Delta$) is the time duration of the STE sequence of the NMR measurement carried out by the logging tool 10.

Thus, in this example, the parameters N, $\delta_{PFG}$, and $g_{PFG}$ are constrained such that the integral of the time-varying amplitude of the N gradient pulses is equal to the integral of the fixed amplitude of the fixed field gradient over its duration (given by $g_{FFG}*T_d$) in the corresponding sequence measured by the downhole tool 10. The parameters $\delta_{PFG}$ and $g_{PFG}$, as well as the timing of the N gradient field pulses are thus generated by the computer 171 and loaded by the test setup routine to the waveform generator circuit block 133 for programming the desired pulsed-mode gradient field to be emitted by the gradient coils 115A, 115B.

Importantly, the duration $\delta_{PFG}$ of the N gradient pulses emitted by the gradient coils 115A, 115B is less than $\tau_{STE}$ in order to allow the magnetic field to stabilize prior to the next RF pulse (or signal acquisition event). Moreover, the gradient pulses emitted by the gradient coils 115A, 115B of the laboratory apparatus 101 do not overlap in time with the CPMG pulses emitted by the RF antenna 117 as well as the receive mode time periods for acquisition of the measured NMR resonance signal by the RF antenna 117. This feature provides the following advantages:

1) the spin dynamics are simplified; notably the application of the CPMG pulses does not generate off-resonance effects such as stimulated echoes; and 2) the spin echoes are not narrowed significantly by magnetic field inhomogeneities, providing a longer receive-mode acquisition window and hence improved signal-to-noise ratio.

These advantages simplify the data acquisition and analysis.

It is typical that the inherent signal-to-noise ratio (SNR) of the NMR measurements carried out by the laboratory apparatus 101 is greater than the SNR of the NMR measurements carried out by the downhole logging tool 10. The differences between the SNR of the laboratory apparatus 101 and the downhole logging tool 10 can lead to discrepancies between the NMR measurements carried out by the respective tools and thus make comparison of such NMR measurements difficult. Importantly, the SNR introduces effects into the NMR measurements and resulting analysis that are complicated in nature (i.e., not a simple scaling effect). Moreover, the SNR of the NMR measurements carried out by the downhole logging tool 10 can be affected by downhole conditions such as temperature and salinity of the formation sample.

In the preferred embodiment of the present invention, synthetic noise is introduced to the NMR measurements carried out by the laboratory apparatus 101 such that the SNR of these NMR measurements corresponds to the known or expected SNR of the NMR measurements performed by the downhole tool during NMR analysis of corresponding formation samples. The SNR of the downhole tool can be characterized empirically according to its design and possibly as a function of downhole conditions (such as temperature and salinity of the formation sample). Such downhole conditions can be measured or estimated by downhole fluid analysis of the formation sample. The NMR measurement data generated by the NMR measurement routine, which is degraded by the synthetic noise, is then interpreted to determine one or more petrophysical parameters (for example, remaining oil saturation ($S_{or}$)) expressed by the NMR measurement data. The one or more petrophysical parameters derived from the NMR measurement data is then compared to corresponding "ground truth" petrophysical parameter(s) that are derived from laboratory measurements not reliant upon NMR measurements (and assumed accurate for the purposes herein). The result of the comparison is used to determine an accuracy estimate for the parameter interpretation(s). This accuracy estimate is predictive of the actual performance of the NMR measurements carried out by the downhole logging tool 10. In this manner, the synthetic noise characteristic of the downhole logging tool 10 is used by the laboratory apparatus 101 to predict the actual performance of the NMR measurements carried out by the downhole logging tool 10. The accuracy estimate can be used to update the NMR protocols, parameter settings, averaging times (or number of repeat measurements)

carried out by the downhole logging tool 10, if necessary. This provides for planning and tuning of the NMR analysis carried out by the downhole tool to ensure desired accuracy, resolution, or discrimination in the properties measured by the downhole logging tool 10.

Figure 13A:
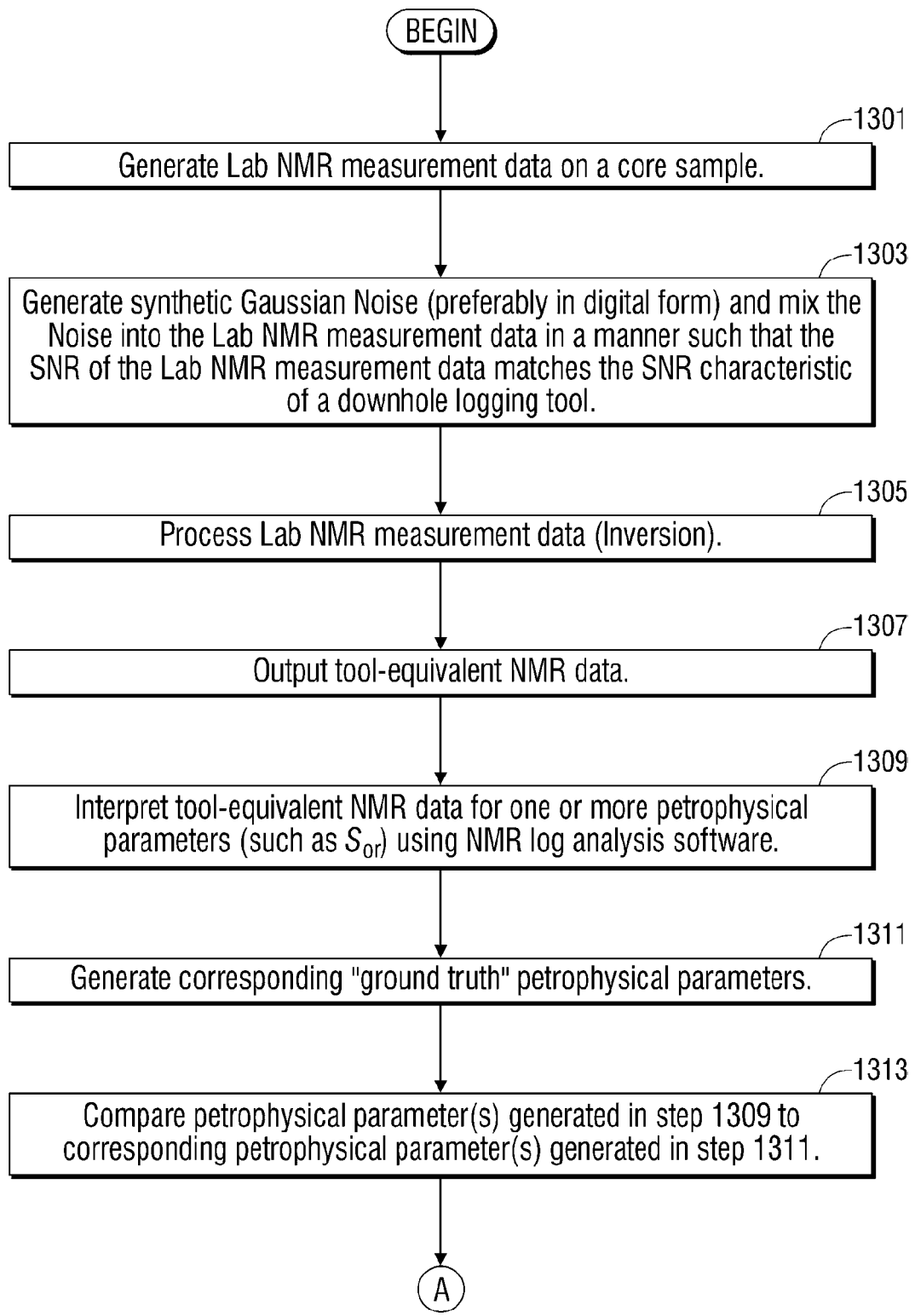
FIGS. 13A and 13B, collectively, are a flow chart of an exemplary workflow employing synthetic noise characteristic of a downhole tool as part of laboratory NMR analysis to predict the actual performance of the NMR measurements carried out by the downhole tool. The workflow provides for evaluation and update of the variables of the NMR analysis carried out by the downhole tool in order to meet desired accuracy.
Figure 13B:
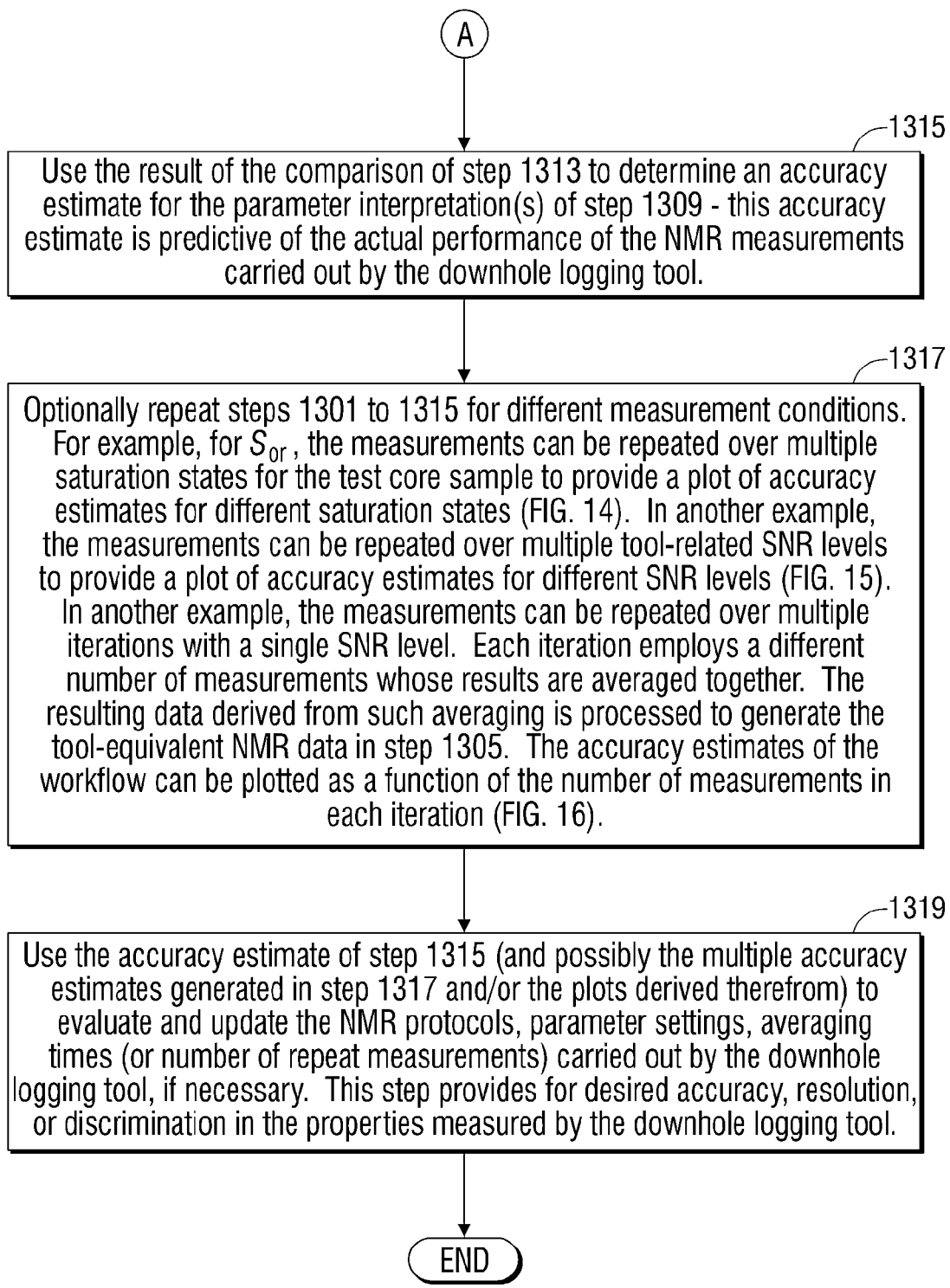

An exemplary workflow employing the synthetic noise characteristic of a downhole logging tool as part of laboratory NMR analysis is shown in FIGS. 13A and 13B. In step 1301, the laboratory apparatus 101 is used to carry out NMR analysis on a core sample and generate lab NMR measurement data as described herein. In step 1303, synthetic Gaussian noise is introduced to the lab NMR measurement data. The synthetic noise (in digital form) can be generated by the processing platform of computer 171 and mixed with the lab NMR measurement data input by the NMR measurement routine of FIG. 4. Alternatively, the synthetic noise (in analog form) can be generated by circuitry and mixed into the NMR signals produced by the receiver circuitry 129 for supply to the analog-to-digital conversion block 131 and subsequent input to the processing platform of computer 171 during the NMR measurement routine carried out on the processing platform. The synthetic noise introduced into the lab NMR measurement data degrades such data, providing a SNR for such lab NMR measurement data that corresponds to the known or expected SNR of the NMR measurement data obtained by the downhole logging tool 10 during NMR analysis of corresponding formation samples. It is contemplated that the SNR of the lab NMR measurement data will be equivalent to (or possibly lower than) the known or expected SNR of the NMR measurement data obtained by the downhole logging tool 10.

In step 1305, the lab NMR measurement data is processed (e.g., inversion) by the NMR Data Analysis Module of the apparatus 101 as described herein to derive corresponding tool-equivalent NMR data.

In step 1307, the tool-equivalent NMR data generated in step 1305 is output for use by an NMR log analysis software package. In step 1309, the tool-equivalent NMR data output in step 1307 is interpreted by the NMR log analysis software package to derive one or more petrophysical parameters that are expressed by the tool-equivalent NMR data. For example, one of the petrophysical parameters may be remaining oil saturation ($S_{or}$).

In step 1311, "ground truth" petrophysical parameter(s) corresponding to the petrophysical parameter(s) generated in step 1309 are derived from laboratory measurements not reliant upon NMR measurements (and assumed accurate for the purposes herein).

In step 1313, the petrophysical parameter(s) generated in step 1309 are compared to the petrophysical parameter(s) generated in step 1311.

In step 1315, the result of the comparison of step 1313 is used to determine an accuracy estimate for the parameter interpretation(s) of step 1309. This accuracy estimate is predictive of the actual performance of the NMR measurements carried out by the downhole logging tool 10. In this manner, the synthetic noise characteristic of the downhole logging tool 10 is used by the laboratory apparatus 101 to predict the actual performance of the NMR measurements carried out by the downhole logging tool 10.

Figure 14:
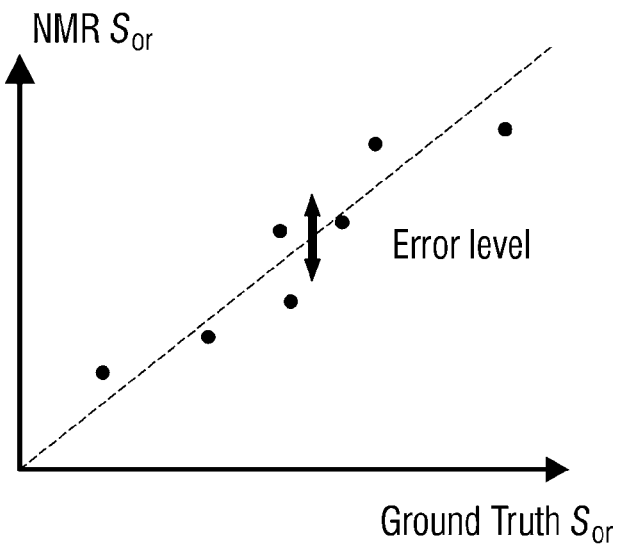
FIG. 14 is a scatter plot of remaining oil saturation ($S_{or}$) derived from laboratory NMR analysis impaired by synthetic noise as well as the "ground truth" $S_{or}$ (dotted line) for different saturation states, which is produced as part of the workflow of FIGS. 13A and 13B.
Figure 15:
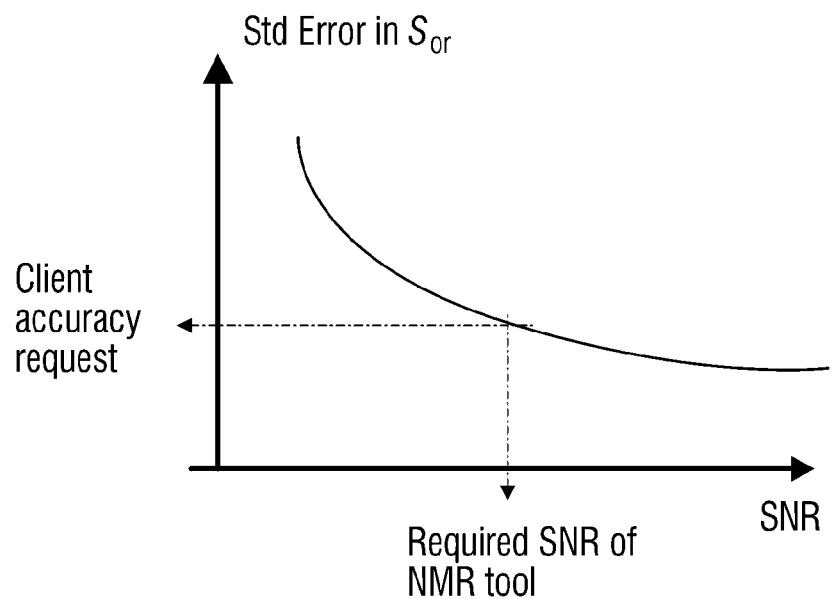
FIG. 15 is a plot of accuracy estimates of $S_{or}$ derived from laboratory NMR analysis impaired by synthetic noise for different signal-to-noise ratio (SNR) levels, which is produced as part of the workflow of FIGS. 13A and 13B.
Figure 16:
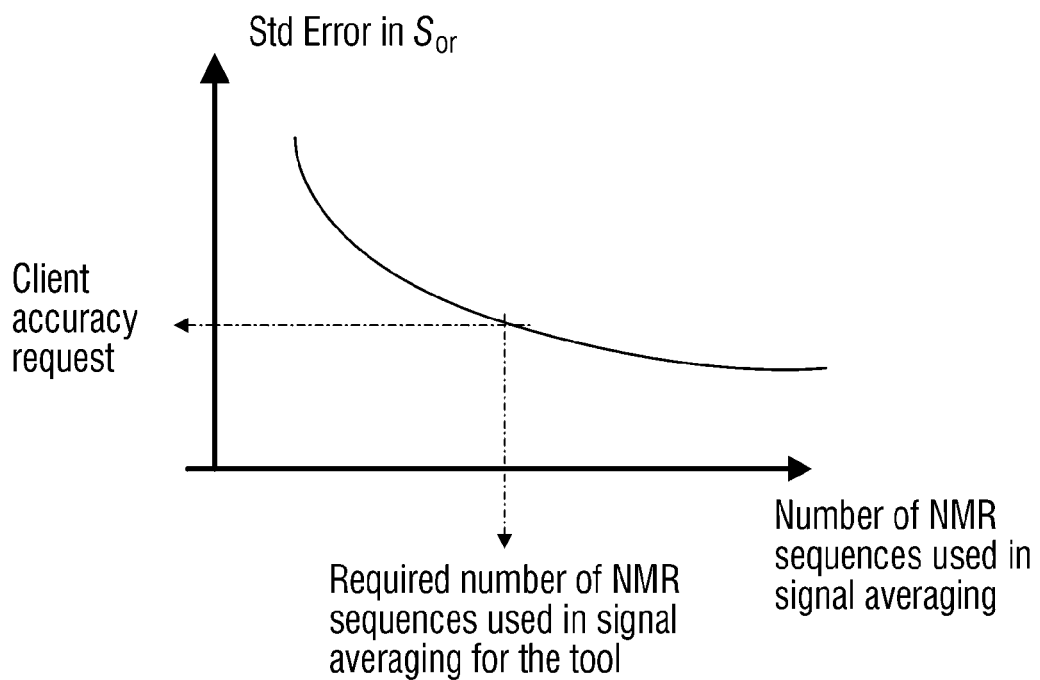
FIG. 16 is a plot of accuracy estimates of $S_{or}$ derived from laboratory NMR analysis impaired by synthetic noise for multiple iterations with a single SNR level, which is produced as part of the workflow of FIGS. 13A and 13B. Each iteration employs a varying number of NMR sequences whose results are averaged together. The accuracy estimates of the workflow are plotted as a function of the number of NMR sequences in each iteration.

Optionally, in step 1317, steps 1301 to 1315 can be repeated for different measurement conditions. For example, for $S_{or}$, the measurements can be repeated over multiple saturation states for the test core sample to provide a scatter plot of the measured $S_{or}$ as well as the "ground truth" $S_{or}$ (dashed-line) for different saturation states (FIG. 14). The accuracy estimates are represented by the distance between the points and the dashed-line. In another example, the measurements can be repeated over multiple tool-related SNR levels to provide a plot of accuracy estimates for different SNR levels (FIG. 15). In yet another example, the measurements can be repeated over multiple iterations with a single SNR level. Each iteration employs a varying number of NMR sequences (measurements) whose results are averaged together. This technique is common for downhole NMR tools as the signal averaging over multiple NMR sequences improves the SNR of the NMR measurement. The resulting data derived from such averaging is processed to generate the tool-equivalent NMR data in step 1305 of the workflow. The accuracy estimates of the workflow can be plotted as a function of the number of measurements in each iteration (FIG. 16).

In step 1319, the accuracy estimate generated in step 1315 (and possibly the multiple accuracy estimates generated in step 1317 and/or the plots derived therefrom) are used to evaluate and update the NMR protocols, parameter settings, averaging times (or number of repeat measurements) carried out by the downhole logging tool 10, if necessary. This provides for planning and tuning of the NMR analysis carried out by the downhole logging tool 10 to ensure desired accuracy, resolution, or discrimination in the properties measured by the downhole logging tool 10.

As described above, the data analysis of the NMR data measured by the logging tool 10 as well as the data analysis performed by the NMR Data Analysis module of the laboratory apparatus 101 can employ an inversion methodology for deriving 2-D distribution function $f(D,T_2)$ relating the diffusion coefficient D to the spin-spin ($T_2$) relaxation times of the sample.

Such inversion can be performed using Tikhonov regularization. Often, it is assumed that the two dimensions (x, y) of the data exhibit Tensor product structure and therefore the exponential kernels $k_{1,2}$ of the underlying function $f(x,y)$ are separable. This assumption allows the $K_{1,2}$ matrices to be handled independently, reducing the computational complexity of the inversion. The data can be compressed to the form of a linear Fredholm integral using Singular Value Decomposition (SVD) of the kernel matrices. This optimization can be achieved using a combination of truncation of the number of singular values, a non-negative constraint, and a smoothing parameter that is chosen according to one of several equivalent methods, including but not limited to S-curve, Butler-Reeds-Dawson (BRD), and generalized cross validation (GCV) methods. The S-curve method is described in P. C. Hansen, "Analysis of discrete ill-posed problems by means of the L-curve," SIAM Rev., Vol. 34, No. 4, December 1992, pgs. 561-580. The BRD method is described in J. P. Butler et al., "Estimating Solutions of First Kind Integral Equations with Nonnegative Constraints and Optimal Smoothing," SIAM Journal on Numerical Analysis, vol. 18, No. 3, 1981, pp. 381-397. The GCV method is described in G. Wahba, "Practical Approximate Solutions to Linear Operator Equations When the Data are Noisy," SIAM Journal on Numerical Analysis, vol. 14, 1977, pp. 651-667, and J. D. Wilson, "Statistical Approach to the Solution of the First Kind Integral Equations Arising in the Study of Materials and their Properties," Journal of Materials Science, vol. 27, July 1992, pp. 3911-3924. In the case of the two dimensional function $f(D, T_2)$ generated by diffusion editing pulse sequences (FIG. 3 and FIG. 5), this is not true because the initial echo amplitudes are attenuated by both diffusion and relaxation. The kernels can be made separable with the change of variable $$t' = 2t_{E,1} + n t_E \qquad (3)$$

where $2t_{E,1}$ is the echo spacing $2\tau_{STE}$ of the echo of the STE sequence, $t_E$ is the echo spacing for the CPMG echo train, and n is the echo index of the CPMG echo train.

Thus, the amplitude M of the echo strength can be represented as $$M(t_{E,1},t') = \iint k_1(D_{eff},t_{E,1})k_2(T_2,t')f(D_{eff},T_2)dD_{eff}dT_2 + E(t_{E,1},t') \quad (4)$$

where $E(t_{E,1},t')$ is experimental noise (error).

Figure 6A:
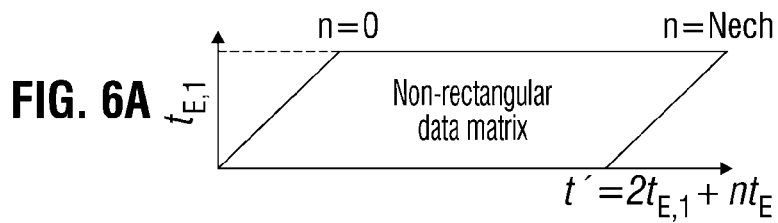
FIG. 6A is a pictorial illustration of a non-rectangular data matrix.
Figure 6B:
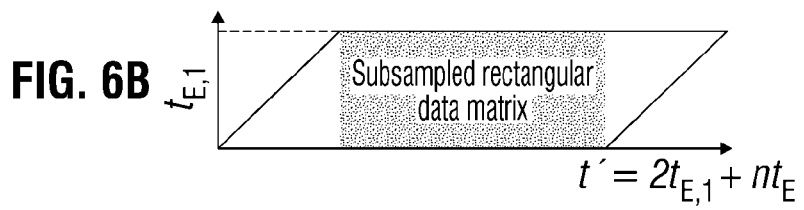
FIG. 6B is a pictorial illustration depicting truncation of the non-rectangular data matrix of FIG. 6A.
Figure 6C:
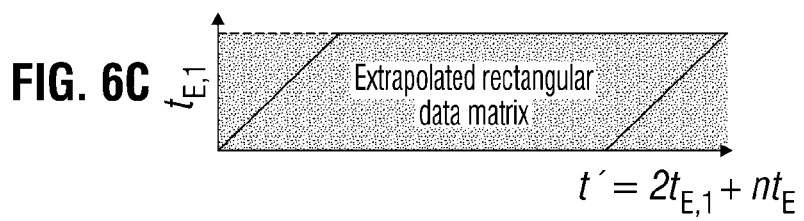
FIG. 6C is a pictorial illustration depicting extrapolation of the non-rectangular data matrix of FIG. 6A.

Following the change of variable, the data is no longer on a rectangular grid as shown in FIG. 6A. In order to invert the data, the data must be modified in one of two possible ways. One way is truncating the data into a rectangular grid as illustrated in FIG. 6B, where the time points of the data in the second ($T_2$) dimension are equal. This results in loss of data with the highest signal-to-noise ratio. The other way is extrapolating the data onto a rectangular grid as illustrated in FIG. 6C. This extrapolation can result in the generation of artificial relaxation time components.

Alternatively, the inversion can be achieved by assuming the data does not exhibit Tensor product structure so that the exponential kernels $k_{1,2}$ of the underlying function f(x,y) are non-separable. In this case, the amplitude M of the echo strength can be represented as $$M(t_{E,1},nt_E) = \iint k_0(D_{eff},T_2,t_{E,1},nt_E)f(D_{eff},T_2)dD_{eff}dT_2 + E(t_{E,1},nt_E) \quad (5)$$

where $k_0$ is the Kronecker product of $k_1$ and $k_2$ such that $k_0 = k_1 \otimes k_2$.

In this case, the kernels $k_{1,2}$ share the variable $t_{E,1}$. For the exemplary embodiment of the CPMG sequence with fixed field gradient as shown in FIG. 3, $k_0$ can be represented by $$k_0 = \exp\left[-\frac{1}{6}\gamma^2 g^2 D_{eff} t_{E,1}^3\right]\exp\left[-\frac{2t_{E,1}}{T_2}\right]\exp\left[-\frac{nt_E}{T_2}\right]. \quad (6)$$

For the exemplary embodiment of the CPMG sequence with pulsed-mode gradient as shown in FIG. 5, $k_0$ can be represented by $$k_0 = \exp\left[-\gamma^2 g^2 D_{eff}\frac{\delta(2t_{E,1}-\delta)}{\pi^2}\right]\exp\left[-\frac{2t_{E,1}+nt_E}{T_2}\right]. \quad (7)$$

The kernel can be modified for different gradient pulse shapes as described in W. S. Price, "Pulse-field Gradient Nuclear Magnetic Resonance as a Tool for Studying Translational Diffusion: Part II. Experimental Aspects," Concepts in Magnetic Resonance, vol. 10, 1998, pp. 197-237.

Equation (5) can be expressed in matrix notation as $M=K_0F+E$. In this implementation, the full $K_0$ matrix can be generated as described in U.S. Pat. No. 6,937,014, incorporated herein by reference. This allows non-rectangular data arrays (FIG. 6A) to be inverted. However, this matrix can contain a large number of values; for example, if the acquired data M ($t_{E,1},nt_E$) contains i×j data points, and the output correlation function f(D, $T_2$) contains m×n data points, then the $K_0$ matrix will contain i×j×m×n data points. It is common to generate very large numbers of echoes in the portion of the CPMG sequence that encodes for the transverse relaxation time $T_2$, e.g. j~40,000. The size of the input data array can be reduced by taking windowed averages of the echo intensities or simply decimating the data (e.g., selecting 32 echoes on a log time base from the echo train). Due to the nature of the numerical inversion, this reduction in input data has little impact on the output correlation, assuming the input data array size is reduced in an appropriate manner. A typical desktop computer running a 32-bit operating system can typically generate the $K_0$ matrix based on an input data size of 32×32 and an output correlation size of 64×64. A larger $K_0$ matrix can be generated using 64-bit operating systems, although the time required to generate the singular values of the $K_0$ matrix necessary for data compression may become excessively long.

The BRD method of choosing the optimum smoothing parameter α for the numerical inversion requires the standard deviation of the noise on the data. If the signal-to-noise ratio is very high, α→0. Hence no smoothing is applied and the output contains additional artifacts determined by noise or systematic errors in the data. It is also possible to use the Generalized Cross Validation (GCV) method, which is described in detail in G. Wahba, "Practical Approximate Solutions to Linear Operator Equations When the Data are Noisy," SIAM Journal on Numerical Analysis, vol. 14, 1977, pp. 651-667, and J. D. Wilson, "Statistical Approach to the Solution of the First Kind Integral Equations Arising in the Study of Materials and their Properties," Journal of Materials Science, vol. 27, July 1992, pp. 3911-3924. This method does not require the standard deviation of the noise on the data.

The operation of the STE-CPMG sequence with the pulsed-mode gradient of FIG. 5 has been demonstrated on four samples: deionized water doped with nickel chloride, hexadecane, a water saturated Portland limestone rock core, and a brine (2 weight percent potassium chloride solution) saturated Bentheimer sandstone rock core. The sandstone was saturated with brine to prevent osmotic swelling of the clay content. The data were acquired using an Oxford Instruments Maran DRX bench-top spectrometer operating at a resonant frequency $f_0$=2 MHz, with a three dimensional gradient set capable of supplying a maximum gradient of $g_{max}$=0.5 T/m on each of the x, y, and z axes. The CPMG sequence with the pulsed-mode gradient of FIG. 5 was implemented with the duration of the sinusoidal magnetic field gradient pulses varying between $\delta_{PFG}$=400 μs to 8 ms, and a maximum amplitude $g_{PFG}$ of 0.3 T/m applied on the y axis. This is equivalent to a fixed field gradient of $g_{PFG}$=0.191 T/m over a total acquisition time of approximately 2 seconds. In the portion of the NMR sequence encoding the transverse relaxation time, 3333 echoes were acquired with an echo time $t_E$=600 ms.

Figure 7:
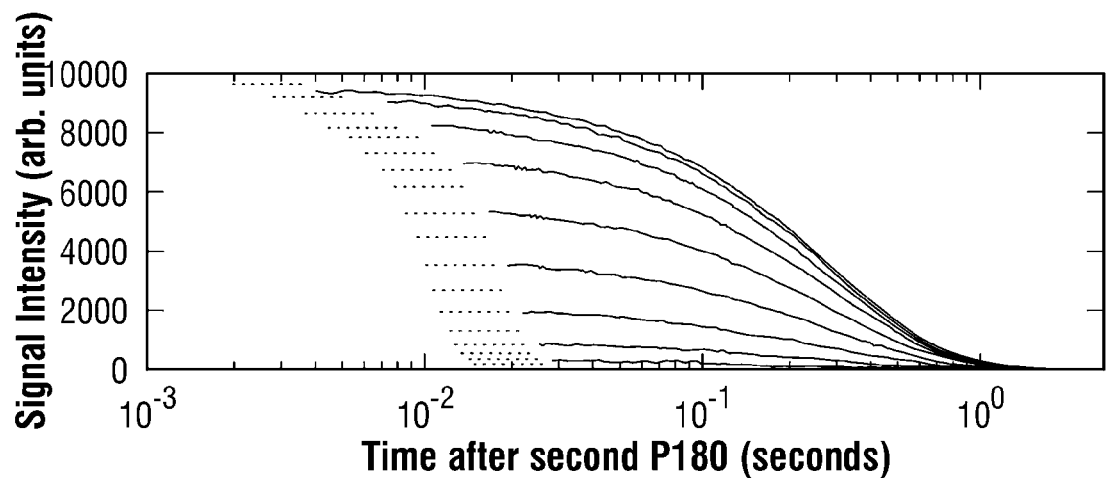
FIG. 7 shows data acquired from NMR analysis of a sample of water doped with nickel chloride carried out by a bench-top NMR tool (similar to that shown in FIG. 4) utilizing a Carr-Purcell-Meiboom-Gill (CPMG) sequence with pulse field gradient (similar to that shown in FIG. 5).

FIG. 7 shows the raw data acquired from a sample of water doped with nickel chloride. The solid lines represent diffusion weighted $T_2$ relaxation decays (CPMG spin echo trains) with magnetic pulse lengths of (top to bottom) $\delta_{PFG}$=400 μs to 8000 μs. The dotted lines indicate the intensity of the first direct echo in each data set. Note that each of the CPMG decays starts at a different time, determined by $2t_{E,1}$. The initial echo intensity is diffusion weighted and so the amplitude decreases as δ increases. To highlight the diffusion attenuation, the amplitudes of the first 3 echoes in each CPMG decay from FIG. 7 are plotted against the effective diffusion time in FIG. 8. The echo intensities lie almost on straight line in this log-linear plot; a line of best fit has been added to guide the eye. Deviations from this line occur due to the variable $T_2$ weighting in the data, and experimental noise.

Some preliminary results are presented in FIGS. 8 to 12. In each plot a horizontal dashed line indicates the diffusion coefficient of water at 24.15° C., and a diagonal dotted line indicates the temperature-independent diffusion/relaxation correlation for alkanes.

Figure 8:
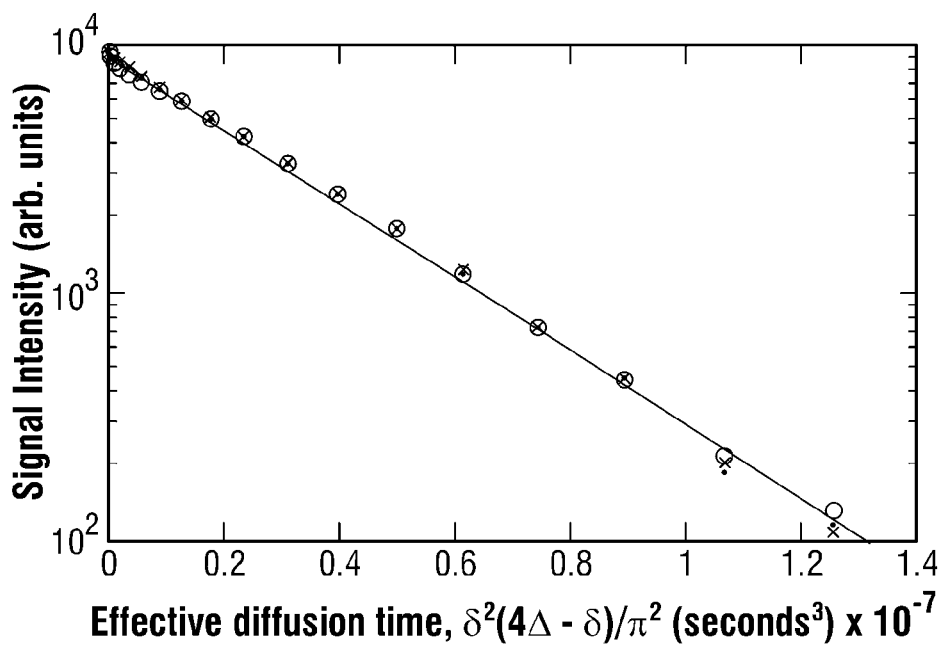
FIG. 8 shows signal attenuation of the first, second, and third spin echoes extracted from the data of FIG. 7.

FIG. 8 shows the D-$T_2$ correlation obtained from a sample of deionized water doped with nickel chloride to reduce the relaxation time. This doping has no effect on the self-diffusion coefficient of the water. However, reducing both the transverse ($T_2$) and longitudinal ($T_1$) relaxation times allows the pulse sequence to be implemented with a shorter recovery delay $T_w=5\times T_1$ between successive scans. For typical deionized water, $T_1=T_2\approx 2$ s. The plot shows a single component observed at A with $D=2.4\times 10^{-9}$ $m^2$ $s^{-1}$ and $T_1=T_2=0.3$ s.

Figure 9:
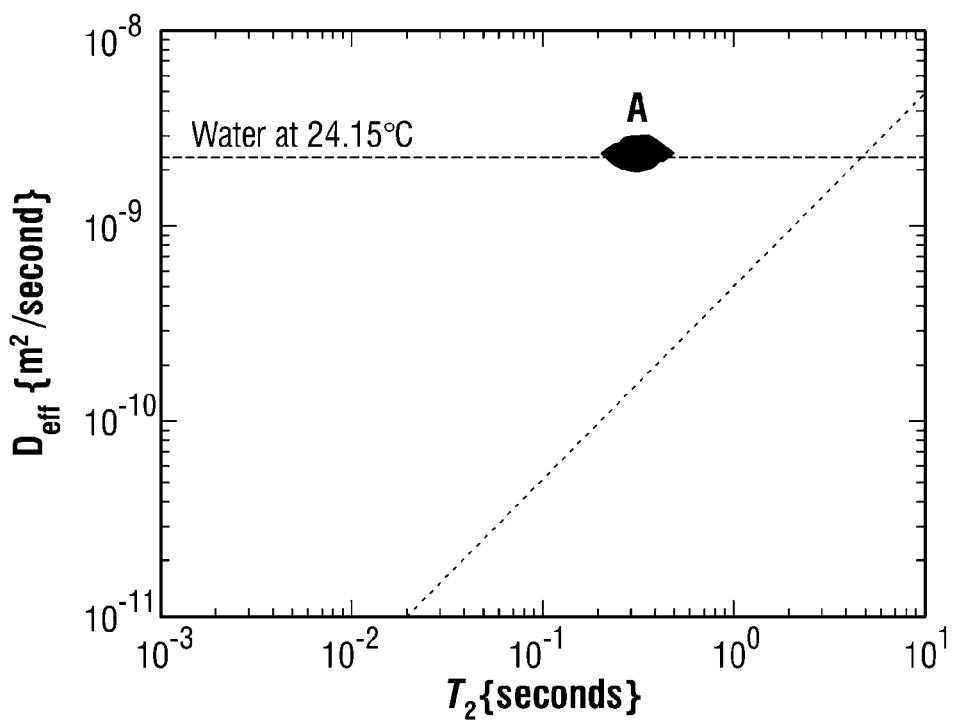
FIG. 9 shows a $D$-$T_2$ correlation for a sample of doped water at ~25° C., which was carried out by a bench-top NMR tool (similar to that shown in FIG. 4) utilizing a CPMG sequence with pulse field gradient (similar to that shown in FIG. 5).

FIG. 9 shows the D-$T_2$ correlation for hexadecane. A single component is observed at A close to the temperature-independent diagonal 'alkane' line, with $D=3.7\times 10^{-9}$ $m^2$ $s^{-1}$ and $T_2=0.6$ s. The $T_2$ relaxation time is slightly lower than predicted due to the presence of paramagnetic molecular oxygen dissolved in the liquid.

Figure 10:
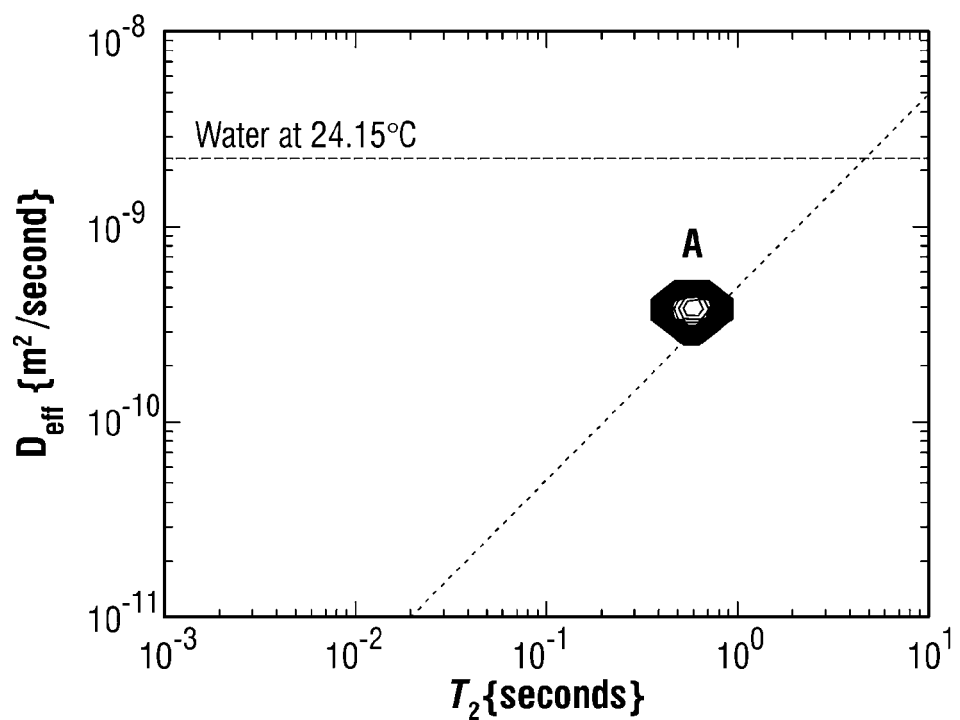
FIG. 10 shows a $D$-$T_2$ correlation for a sample of hexadecane at ~25° C., which was carried out by a bench-top NMR tool (similar to that shown in FIG. 4) utilizing a CPMG sequence with pulse field gradient (similar to that shown in FIG. 5).

A critical property of the D-$T_2$ sequence is the ability to distinguish oil and water. FIGS. 9 and 10 demonstrate that the CPMG sequence of FIG. 5 can provide correct relaxation times and diffusion coefficients over several orders of magnitude and hence be used for characterization of oil and water fractions in reservoir rock cores.

Figure 11:
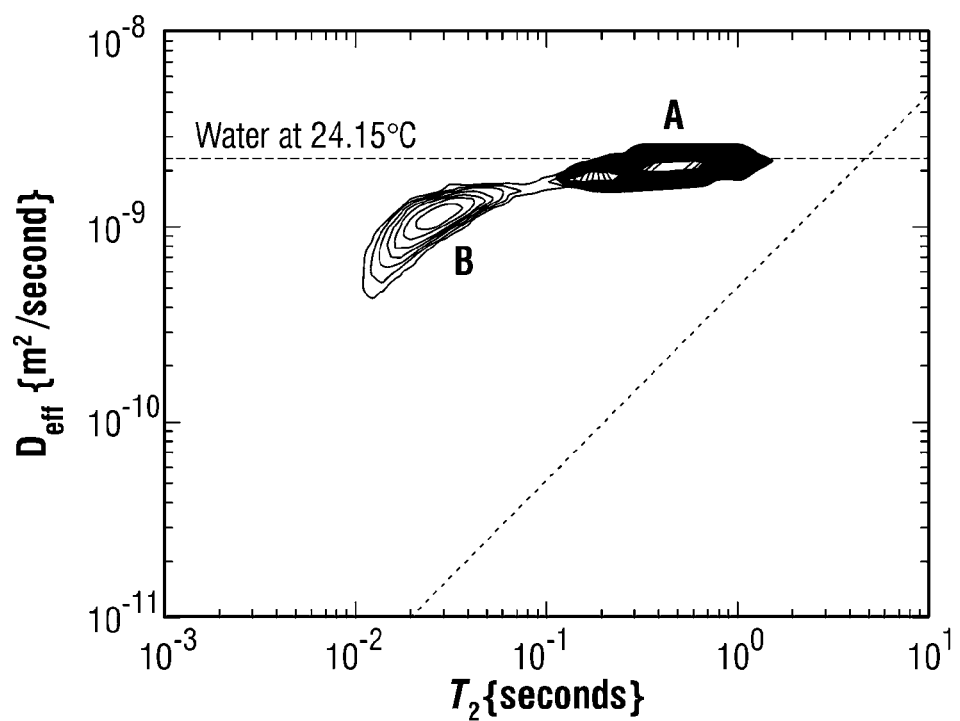
FIG. 11 shows a $D$-$T_2$ correlation for a sample of water saturated Portland limestone rock core, which was carried out by a bench-top NMR tool (similar to that shown in FIG. 4) utilizing a CPMG sequence with pulse field gradient (similar to that shown in FIG. 5).
Figure 12:
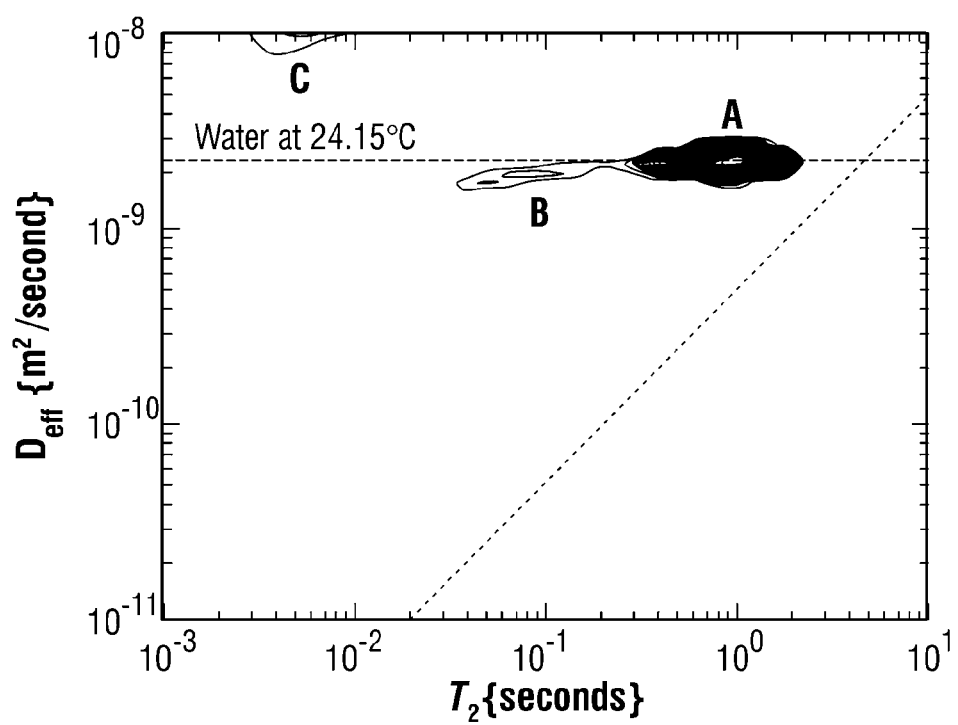
FIG. 12 shows a $D$-$T_2$ correlation for a sample of brine (water) saturated Bentheimer sandstone, which was carried out by a bench-top NMR tool (similar to that shown in FIG. 4) utilizing a CPMG sequence with pulse field gradient (similar to that shown in FIG. 5).

FIGS. 11 and 12 demonstrate the applicability of the CPMG sequence of FIG. 5 to rock core analysis. Although these cores are only saturated with water, the salient features typical of these types of rock are visible. In the Portland limestone (FIG. 11), two discrete components are observed at A and B. The A component corresponds to water in macroscopic pores or cracks (long $T_2$, high apparent diffusivity), while the B component corresponds to water in the microporosity (short $T_2$, reduced apparent diffusivity). The apparent diffusion coefficient is reduced when water is confined in the pores due to the restricted diffusion pathways and tortuosity of the interconnected core network. This is more significant in the smaller pores as expected.

FIG. 12 shows the D-$T_2$ correlation for a brine (water) saturated Bentheimer sandstone. This rock is known to comprise sand grains with a typical diameter of ~100 μm. Consequently, this rock has a very narrow distribution of pore sizes, as reflected by the dominant diffusion/relaxation component observed at A. A small, secondary water component is also observed at B, which is associated either with smaller pores or the influence of the pore surface. Notably, a third water component is observed at C. Such high apparent diffusivities have been noted previously in sandstones, although they are artifacts resulting from the presence of a background magnetic field gradient induced by magnetic susceptibility differences between the solid and liquid (due primarily to the presence of paramagnetic chemical species in the clay components), rather than fast diffusing water molecules.

Advantageously, the methodology of the present invention (and corresponding system and apparatus) provide for NMR measurements and analysis that allow for diffusion-relaxation correlation data to be acquired on a bench-top (laboratory) NMR apparatus in such a way as to allow a direct comparison with equivalent data acquired utilizing an NMR well logging tool. The direct comparison of NMR data sets produced by an NMR well logging tool and bench-top NMR analyzer can be used to calibrate the petrophysical interpretations made of borehole logging measurements, because in the laboratory the operator has access to independent measurements on the same rock and fluid samples. These measurements include (but are not limited to) porosity, pore size distribution, permeability, oil and water saturations, oil viscosity, and indicators of crude oil chemical composition, all of which petrophysical properties influence the NMR signal acquired, and for all of which there are known methods of interpretation in the prior art. The importance of reference measurements arises because most of these interpretation methods (whether for rock properties or for fluid properties) are subject to uncertainties and ambiguities, both in data processing and in the physics of the NMR response, where different rock or fluid properties may give rise to a similar NMR signal or signature. Having access to actual rock and fluid samples in the lab, on which such properties can be determined with much less ambiguity, is thus of great value in interpreting the borehole NMR logs. For some applications, it becomes important to carry out the laboratory NMR measurements under conditions as close as possible to those obtaining in the actual logging tool, because different biases occur for different NMR protocols, and because signal-to-noise ratio may be radically different between laboratory and borehole.

The invention can also be used in a predictive manner to plan a logging program not yet undertaken. In this scenario, the laboratory measurements can be carried out with various choices of parameter, in order to predict the likely response of the rock formations to the NMR logging measurements, and to determine, design, or otherwise optimize the parameter selections required to yield the necessary precision, resolution, or other discrimination required in the measurements for which the borehole logging program is undertaken. This can be done, for example, when rock or fluid samples from the same or a similar rock formation are available already, and believed to possess properties representative of the formation to be studied. Laboratory measurements on such samples can be done to plan the best choice of protocols or parameters that can be made in advance of performing the actual borehole measurements. Having determined an optimum choice of protocol or parameter in the laboratory, these parameters are then transferred to the logging tool when the borehole measurements are made.

A similar planning exercise can be made in preparing for borehole measurements in the observation wells in connection with EOR projects. More particularly, an NMR logging tool can be used to monitor the progress of an EOR project, where injection of gases such as carbon dioxide, methane, or mixtures of such gases with other light hydrocarbons may be used to improve the displacement and recovery of reservoir hydrocarbon. Alternative EOR processes may involve the use chemical surfactants to improve oil recovery by reducing surface tension and detergency. It is normal practice to introduce observation wells in such projects, which are drilled primarily to monitor the process, rather than for producing oil, or injecting the gases or surfactants. NMR is one technology that can be used for such observations, provided the wells are cased with tubulars which are invisible to NMR. An example of such observation wells is described in Patent Publication US 2009/0167302. However, because of the cost of drilling and completing such wells, before the engineering and financial commitment is made, it is important to be able to predict by laboratory study that measurements performed in the borehole will in fact yield the necessary data to perform the required monitoring.

In such observation wells, the basic formation properties will be well known, by coring and logging programs at the time the well is drilled, and from other information known regarding the hydrocarbon-bearing reservoir. In the observation well, it is important to be able to detect and measure changes not in rock properties (which are of course unlikely to change radically) but in fluid properties and fluid content, most obviously in oil saturation remaining at various times during the EOR project. In such applications, it is important to be able to choose protocols, parameter settings and averaging times (or number of repeat measurements required) such that the desired accuracy, resolution, or discrimination in the changes in fluid content or properties will be achieved. In this application, the laboratory measurements may need to be carried out using various different oil saturation states, using a sample holder (core holder) capable of changing the saturation of oil or other fluids by various flow processes. The rock core sample will be chosen to be representative of the most important parts of the rock formation penetrated by the observation well, or may include several such samples in the laboratory measurements. Also, the measurements will likely need to be carried out at temperatures and pressures representative of the actual reservoir, because the NMR properties of the fluids will change with temperature and pressure. The importance of the present invention in this application comes from the ability to predict in advance that changes in oil saturation can be observed with the borehole tool, with the required degree of accuracy, and taking into account the signal-to-noise ratio expected from the tool in the borehole, and the data processing methods that will be used. The best confidence in such planning will come from laboratory measurements that mimic the borehole tool as closely as possible, take account of the signal-to-noise ratio available in the tool (or plan for a necessary degree of averaging) and employ the same data processing methods.

In observation wells of the kind cited, there is also a need to plan the protocols that will be used. Borehole logging in cased observation wells is subject to fewer practical constraints that in "open hole" wells (without casing). In particular, the presence of a casing eliminates the risk of a tool becoming stuck in the mudcake that adheres to the exposed rock surface in an open hole. Also, because the observation well has no other purpose, the length of time that the tool spends in the borehole does not have the same economic cost on impeding other operations. Therefore, the tool can stop for as long as necessary, or employ NMR protocols of long duration that are feasible in the laboratory, but not ordinarily feasible in open hole borehole logging, because of the need for the tool to move continuously, and to minimize overall well log duration.

In another example, the present invention can be used to determine the downhole NMR protocol that is required to achieve a target level of accuracy for one or more reservoir parameters measured by a given NMR downhole logging tool. For example, the SNR of the NMR downhole logging tool can typically be improved by employing signal averaging over multiple NMR sequences. In this aspect of the invention, the SNR of the laboratory NMR apparatus can be degraded with the use of synthetic noise as part of NMR measurements carried out by the laboratory NMR apparatus. Such NMR measurements are processed to derive tool-equivalent NMR data. The tool-equivalent NMR data is interpreted to derive one or more petrophysical parameters expressed by the tool-equivalent NMR data. These one or more petrophysical parameters are compared to corresponding parameters derived from "ground truth" measurements, and the result of the comparison is used to determine an accuracy estimate. The accuracy estimate is derived over multiple iterations with different signal averaging schemes. Analysis of the accuracy estimates over the multiple iterations can be used determine the minimum level of signal averaging for use in the given NMR downhole logging tool in order to achieve the desired accuracy for the one or more reservoir parameters measured by the NMR downhole logging tool.

In yet another example, the present invention can be used to compare reservoir parameters measured by the NMR downhole logging tool and NMR laboratory apparatus in order to verify the level of accuracy or data quality of the reservoir parameters measured by the NMR downhole logging tool, and/or to demonstrate that there are formation properties that are simply not measurable in the downhole context (i.e., under the conditions of the logging operation) by the NMR downhole logging tool.

While particular embodiments of the invention have been described, it is not intended that the invention be limited thereto, as it is intended that the invention be as broad in scope as the art will allow and that the specification be read likewise. Thus, while particular downhole NMR tool designs and particular bench-top (laboratory) NMR apparatus have been disclosed, it will be appreciated that other downhole NMR tool designs and particular bench-top (laboratory) NMR apparatus can be used as well. In addition, while particular downhole CPMG and fixed field gradient NMR protocols have been disclosed, it will be understood that other CPMG and fixed field gradient NMR protocols can be used in the downhole tool. Moreover, while particular laboratory CPMG and pulsed-mode gradient NMR protocols have been disclosed, it will be understood that other laboratory pulsed-mode gradient NMR protocols can be used where such protocols are equivalent to those used by the downhole tool. For example, other suitable pulsed-mode waveforms can be used as a substitute for the uni-polar half-sine waveform for the gradient pulses as described herein. Furthermore, while particular inversion methodologies and data processing analysis has been described for correlating relation and diffusion information from NMR measurements, it will be understood that other inversion methodologies and data processing analysis can be similarly used. It will therefore be appreciated by those skilled in the art that yet other modifications could be made to the provided invention without deviating from its scope as claimed.

What is claimed is:

1. A laboratory apparatus comprising:
means for providing downhole tool data corresponding to a hydrocarbon-bearing sample collected from a given subsurface formation, the downhole tool data including parameters used by a downhole tool during nuclear magnetic resonance (NMR) measurements of the given subsurface formation, the downhole tool data including at least one parameter that represents a time interval pertaining to a pulse sequence that is part of the NMR measurements performed by a downhole tool, the pulse sequence for generating at least one diffusion-encoding echo;
a sample volume; and
measurement means for applying at least one NMR measurement to the sample volume to thereby determine a property of a sample positioned in the sample volume, the at least one NMR measurement applying to the sample volume a homogeneous static magnetic field in conjunction with a pulse sequence of oscillating magnetic field and a pulsed-mode gradient field, wherein the pulsed-mode gradient field is defined by a set of pulses that are equivalent to a fixed field gradient for a corresponding NMR measurement performed by the downhole tool, and wherein the fixed field gradient is defined by the downhole tool data corresponding to the hydrocarbon-bearing sample.

2. A laboratory apparatus according to claim 1, wherein the measurement means includes a radio frequency (RF) antenna for applying the pulse sequence of oscillating magnetic field to the sample volume.

3. A laboratory apparatus according to claim 1, wherein the measurement means includes at least one gradient coil for applying the pulsed-mode gradient field to the sample volume.

4. A laboratory apparatus according to claim 1, wherein the pulse sequence of oscillating magnetic field includes an initial tipping radio frequency (RF) pulse and at least one re-focusing RF pulse.

5. A laboratory apparatus according to claim 1, wherein the at least one NMR measurement receives at least one spin echo from the sample volume for recordation and analysis.

6. A laboratory apparatus according to claim 5, wherein the at least one spin echo encodes for diffusion induced by the pulsed-mode gradient field.

7. A laboratory apparatus according to claim 1, wherein the NMR measurements performed by the downhole tool employ fixed field gradients that have constant amplitude at all times.

8. A laboratory apparatus according to claim 1, wherein the property of the sample comprises at least one diffusion coefficient of the sample derived by an inversion methodology.

9. A laboratory apparatus according to claim 8, wherein the inversion methodology employs a maximum entropy principles (MEP) method.

10. A laboratory apparatus according to claim 8, wherein the inversion methodology corresponds to the inversion methodology carried out in deriving NMR data stored as part of the downhole tool data.

11. A laboratory apparatus according to claim 1, further comprising means for introducing synthetic noise into NMR measurement data derived by NMR analysis of the sample volume such that the signal-to-noise ratio (SNR) of the NMR measurement data corresponds to a predetermined SNR.

12. A laboratory apparatus according to claim 11, wherein the predetermined SNR is characteristic of the NMR measurements of the given subsurface formation performed by the downhole tool.

13. A laboratory apparatus according to claim 1, further comprising means for comparing NMR data derived from the NMR measurements carried out by the laboratory apparatus to NMR data provided as part of the downhole tool data.

14. A laboratory apparatus comprising:
   means for providing downhole tool data corresponding to a hydrocarbon-bearing sample collected from a given subsurface formation, the downhole tool data including parameters used by a downhole tool during nuclear magnetic resonance (NMR) measurements of the given subsurface formation;
   a sample volume; and
   measurement means for applying at least one NMR measurement to the sample volume to thereby determine a property of a sample positioned in the sample volume, the at least one NMR measurement applying to the sample volume a homogeneous static magnetic field in conjunction with a pulse sequence of oscillating magnetic field and a pulsed-mode gradient field, the pulsed-mode gradient field defined by the downhole tool data corresponding to the hydrocarbon-bearing sample, wherein the NMR measurements performed by the downhole tool employ fixed field gradients that have constant amplitude at all times, the pulsed-mode gradient field for a given NMR measurement is defined by a set of pulses that are equivalent to the fixed field gradient for a corresponding NMR measurement performed by the downhole tool, and
   the measurement means includes a gradient pulse programming circuit for programming at least one parameter that defines the set of pulses, the gradient pulse programming circuit adapted to program the at least one parameter such that the integral of the time-varying amplitude of the pulses of the set over the time duration of the pulses of the set matches the product of the constant amplitude of the fixed field gradient and duration for the corresponding NMR measurement performed by the downhole tool.

15. A laboratory apparatus according to claim 14, wherein the at least one parameter comprises maximum amplitude for the set of pulses.

16. A laboratory apparatus according to claim 14, wherein the at least one parameter comprises pulse duration for the set of pulses.

17. A laboratory apparatus according to claim 16, wherein the pulse duration for the set of pulses is constrained by a time interval $\tau$ between an initial radio frequency (RF) tipping pulse and a subsequent re-focusing pulse.

18. A laboratory apparatus according to claim 17, wherein the pulse duration for the set of pulses is less than $\tau$.

19. A laboratory apparatus according to claim 14, wherein the set of pulses are each characterized by a uni-polar half-sine waveform.

20. A laboratory apparatus according to claim 14, wherein the downhole tool data includes at least one parameter that represents a time interval pertaining to a pulse sequence that is part of the NMR measurements performed by a downhole tool, the pulse sequence for generating at least one diffusion-encoding echo, and wherein the pulsed-mode gradient field is based on the at least one parameter.

21. A laboratory apparatus according to claim 20, wherein the pulse sequence for generating at least one diffusion-encoding echo comprises a stimulated echo (STE) sequence represented by a spatial encoding interval $\tau_{STE}$ and a storage interval $\Delta$ stored as part of the downhole tool data, and wherein the pulsed-mode gradient field is based on the spatial encoding interval $\tau_{STE}$ and the storage interval $\Delta$.

22. A laboratory apparatus according to claim 14, wherein the downhole tool data includes at least one parameter that represents the fixed field gradient, and the pulsed-mode gradient field is based on the at least one parameter.

23. A laboratory apparatus comprising:
   means for providing downhole tool data corresponding to a hydrocarbon-bearing sample collected from a given subsurface formation, the downhole tool data including parameters used by a downhole tool during nuclear magnetic resonance (NMR) measurements of the given subsurface formation;
   a sample volume; and
   measurement means for applying at least one NMR measurement to the sample volume to thereby determine a property of a sample positioned in the sample volume, wherein the property of the sample comprises at least one diffusion coefficient of the sample derived by an inversion methodology, the at least one NMR measurement applying to the sample volume a homogeneous static magnetic field in conjunction with a pulse sequence of oscillating magnetic field and a pulsed-mode gradient field, the pulsed-mode gradient field defined by the downhole tool data corresponding to the hydrocarbon-bearing sample, and wherein the inversion methodology derives a multidimensional distribution function selected from the group including:
   i) a two dimensional distribution function f(D, T2) relating diffusion coefficient D to the spin-spin (T2) relaxation times of the sample;
   ii) a two dimensional distribution function f (D, T1) relating diffusion coefficient D to the spin-lattice (T1) relaxation times of the sample;
   iii) a three dimensional distribution function f(D, T1, T2) relating diffusion coefficient D to the spin-lattice (T1) relaxation times of the sample and the spin-spin (T2) relaxation times of the sample.

24. A laboratory apparatus comprising:

means for providing downhole tool data corresponding to a hydrocarbon-bearing sample collected from a given subsurface formation, the downhole tool data including parameters used by a downhole tool during nuclear magnetic resonance (NMR) measurements of the given subsurface formation;

a sample volume;

measurement means for applying at least one NMR measurement to the sample volume to thereby determine a property of a sample positioned in the sample volume, the at least one NMR measurement applying to the sample volume a homogeneous static magnetic field in conjunction with a pulse sequence of oscillating magnetic field and a pulsed-mode gradient field, the pulsed-mode gradient field defined by the downhole tool data corresponding to the hydrocarbon-bearing sample;

means for introducing synthetic noise into NMR measurement data derived by NMR analysis of the sample volume such that the signal-to-noise ratio (SNR) of the NMR measurement data corresponds to a predetermined SNR;

means for processing said NMR measurement data derived from NMR analysis of the sample volume to generate tool-equivalent data;

means for interpreting the tool-equivalent data to derive at least one petrophysical parameter expressed by the tool-equivalent data;

means for comparing the at least one petrophysical parameter to a corresponding petrophysical parameter derived from a ground truth-type measurement; and means for determining an accuracy estimate based on the result of the comparing means, the accuracy estimate for use in evaluating and updating variables of the NMR analysis carried out by the downhole tool.

25. A laboratory apparatus according to claim 24, wherein the processing means, interpreting means and comparing means are operated under different measurement conditions in order to derive a plurality of accuracy estimates for the different measurement conditions, the plurality of accuracy estimates for use in evaluating and updating variables of the NMR analysis carried out by the downhole tool.

* * * * *